US008637493B2

(12) United States Patent
Ross et al.

(10) Patent No.: US 8,637,493 B2
(45) Date of Patent: Jan. 28, 2014

(54) METHODS FOR TREATING GLIOBLASTOMA

(75) Inventors: Alonzo H. Ross, Shrewsbury, MA (US); Candace Gilbert, Worcester, MA (US); Richard Moser, Worcester, MA (US)

(73) Assignee: University of Massachusetts, Shrewsbury, MA (US)

( * ) Notice: Subject to any disclaimer, the term of this patent is extended or adjusted under 35 U.S.C. 154(b) by 56 days.

(21) Appl. No.: 12/943,666

(22) Filed: Nov. 10, 2010

(65) Prior Publication Data
US 2011/0178046 A1 Jul. 21, 2011

Related U.S. Application Data

(60) Provisional application No. 61/260,487, filed on Nov. 12, 2009.

(51) Int. Cl.
*A61K 31/63* (2006.01)
*A61K 31/4188* (2006.01)
*A61K 31/175* (2006.01)
*A61K 31/553* (2006.01)
*A61P 35/00* (2006.01)

(52) U.S. Cl.
USPC ....... 514/155; 514/211.09; 514/393; 514/589

(58) Field of Classification Search
USPC .............................. 514/155, 211.09, 393, 589
See application file for complete search history.

(56) References Cited

U.S. PATENT DOCUMENTS

| 6,251,886 | B1 * | 6/2001 | Friedman | 514/183 |
| 2008/0058316 | A1 * | 3/2008 | Eberhart et al. | 514/221 |
| 2008/0220416 | A1 | 9/2008 | Miele et al. | |

OTHER PUBLICATIONS

Joshi et al., Notch signaling mediates G1/S cell-cycle progression in T cells via cyclin D3 and its dependent kinases, Blood, Feb. 19, 2009, vol. 113, No. 8, 1689-1698.*
Bao et al., "Glioma stem cells promote radioresistance by preferential activation of the DNA damage response," Nature, 444(7120):756-760 (2006).
Barten et al., "Gamma-secretase inhibitors for Alzheimer's disease: balancing efficacy and toxicity," Drugs, 7 (2): 87-97 (2006).
Beel and Sanders, "Substrate Specificity of γ-Secretase and Other Intramembrane Proteases," Cell Mol. Life Science, 65(9): 1311-1334 (2008).
"CBTRUS Statistical Report: Primary Brain and Central Nervous system Tumors Diagnosed in the United States in 2004-2006." Hinsdale, IL: Central Brain Tumor Registry of the United States (2010).
Chalmers et al., "Cytotoxic effects of temozolomide and radiation are additive- and schedule-dependent," Int. J. Radiat. Oncol. Biol. Phys., 75(5): 1511-1519 (2009).
Cho et al., "Notch regulates cytolytic effector function in CD8+ T cells," J. Immunol , 182(6): 3380-3389 (2009).
Cullion et al., "Targeting the Notch1 and mTOR pathways in a mouse T-ALL model," Blood, 113(24): 6172-6181 (2009).
Ernst et al., "Genomic and expression profiling of glioblastoma stem cell-like spheroid cultures identifies novel tumor-relevant genes associated with survival," Clin. Cancer Research, 15(21): 6541-6550 (2009).
Fan et al., "Notch pathway inhibition depletes stem-like cells and blocks engraftment in embryonal brain tumors," Cancer Research, 66(15): 7445-7452 (2006).
Fan et al., "NOTCH Pathway Blockade Depletes CD133-Positive Glioblastoma Cells and Inhibits Growth of Tumor Neurospheres and Xenografts," Stem Cells, 28(1): 5-16 (2010).
Fauq et al., "A multigram chemical synthesis of the γ-secretase inhibitor LY411575 and its diastereoisomers," Bioorg. Med. Chem. Lett., 17(22): 6392-6395(2007).
Fleisher et al., "Phase II safety trial targeting amyloid beta production with a gamma-secretase inhibitor in Alzheimer's disease," Arch. Neurol., 65(8): 1031-1038 (2008).
Foroni et al., "Resilience to transformation and inherent genetic and functional stability of adult neural stem cells ex vivo," Cancer Research, 67(8): 3725-33 (2007).
Fukushima et al., "Anti-glioma therapy with temozolomide and status of the DNA-repair gene MGMT," Anticancer Research, 29(11): 4845-54 (2009).
Gilbert et al., "Cancer Stem Cells: Cell Culture, Markers and Targets for New Therapies," J. Cell. Biochem., 108(5): 1031-1038 (2009).
Graziani et al., "Opposite effects of Notch-1 and Notch-2 on mesothelioma cell survival under hypoxia are exerted through the Akt pathway," Cancer Research, 68(23): 9678-85 (2008).
Ivanov et al., "Genes required for *Drosophila* nervous system development identified by RNA interference," PNAS, 101(46): 16216-16221 (2004).
Jeon et al , "Inhibitor of differentiation 4 drives brain tumor-initiating cell genesis through cyclin E and notch signaling," Genes & Development, 22:2028-2033 (2008).
Joshi et al., "Notch signaling mediates G1/S cell-cycle progression in T cells via cyclin D3 and its dependent kinases," Blood, 113(8): 1689-1698 (2009).
Kanamori et al., "Contribution of Notch signaling activation to human glioblastoma multiforme," J. Neurosurg., 106(3): 417-427 (2007).
Kang et al., "Tumorigenesis of chemotherapeutic drug-resistant cancer stem-like cells in brain glioma," Stem Cells Dev., 16(5): 837-847 (2007).
Kreft et al., "Recent advances in the identification of gamma-secretase inhibitors to clinically test the Abeta oligomer hypothesis of Alzheimer's disease," J. Med. Chem., 52(20): 6169-6188 (2009).
Lanz et al., "Concentration-dependent modulation of amyloid-beta in vivo and in vitro using the gamma-secretase inhibitor, LY-450139," J. Pharmacol. Exp Ther., 319(2): 924-933 (2006).

(Continued)

*Primary Examiner* — Yong Chong
*Assistant Examiner* — Jason A Deck
(74) *Attorney, Agent, or Firm* — Fish & Richardson P.C.

(57) ABSTRACT

Described are methods for treating cancers, e.g., glioblastoma, including administering an inhibitor of Notch signalling, e.g., a gamma secretase inhibitor, in combination with a chemotherapeutic agent.

15 Claims, 15 Drawing Sheets

(56) References Cited

OTHER PUBLICATIONS

Lee et al., "Tumor stem cells derived from glioblastomas cultured in bFGF and EGF more closely mirror the phenotype and genotype of primary tumors than do serum-cultured cell lines," Cancer Cell, 9(5): 391-403 (2006).

Liu et al., "Analysis of gene expression and chemoresistance of CD133+ cancer stem cells in glioblastoma," Molecular Cancer, 5:67 (2006).

Mihaliak et al., "Clinically relevant doses of chemotherapy agents reversibly block formation of glioblastoma neurospheres," Cancer Left., 296(2):168-177 (2010).

Namihira et al., "Committed neuronal precursors confer astrocytic potential on residual neural precursor cells," Dev. Cell, 16(2): 245-255 (2009).

Olson and Albright, "Recent progress in the medicinal chemistry of gamma-secretase inhibitors," Curr. Top Med. Chem., 8(1): 17-33 (2008).

Ostermann et al., "Plasma and cerebrospinal fluid population pharmacokinetics of temozolomide in malignant glioma patients," Clin. Cancer Research, 10(11): 3728-3736 (2004).

Patzel et al., "Design of siRNAs producing unstructured guide-RNAs results in improved RNA interference efficiency," Nat. Biotechnol., 23(11): 1440-1444(2005).

Presente et al., "Notch is required for long-term memory in *Drosophila*," PNAS,101(6):1764-1768 (2004).

Pui et al., "Notch1 expression in early lymphopoiesis influences B versus T lineage determination," Immunity, 11(3): 299-308 (1999).

Purow et al. "Expression of Notch-1 and Its Ligands, Delta-Like-1 and Jagged-1, Is Critical for Glioma Cell Survival and Proliferation," Cancer Res., 65(6):2353-2363 (2005).

Rao et al., "Inhibition of NOTCH signaling by gamma secretase inhibitor engages the RB pathway and elicits cell cycle exit in T-cell acute lymphoblastic leukemia cells," Cancer Research, 69:3060-3068 (2009).

Reynolds and Weiss, "Clonal and population analyses demonstrate that an EGF-responsive mammalian embryonic CNS precursor is a stem cell," Dev. Biol., 175(1): 1-13 (1996).

Rizzo et al., "Rational targeting of Notch signaling in cancer," Oncogene, 27(38): 5124-5131 (2008).

Samon et al., "Notch1 and TGFβ1 cooperatively regulate Foxp3 expression and the maintenance of peripheral regulatory T cells," Blood, 112(5): 1813-1821 (2008).

Sang et al., "Control of the reversibility of cellular quiescence by the transcriptional repressor HES1," Science, 321(5892): 1095-1100 (2008).

Sharma et al., "Notch1 Contributes to Mouse T-Cell Leukemia by Directly Inducing the Expression of c-myc," Mol. Cell. Biol., 26(21): 8022-8031 (2006).

Sherry et al., "STAT3 is required for proliferation and maintenance of multipotency in glioblastoma stem cells," Stem Cells, 27(10): 2383-2392 (2009).

Shih et al. "Notch Signaling Enhances Nestin Expression in Gliomas1," Neoplasia, 8(12):1072- 1082 (2006).

Singh et al., "Identification of a Cancer Stem Cell in Human Brain Tumors," Cancer Research, 63:5821-5828 (2003).

Spilman et al., "A γ-secretase inhibitor and quinacrine reduce prions and prevent dendritic degeneration in murine brains," PNAS,105(30):10595-10600 (2008).

Stanwood et al., "Small Interfering RNA-Mediated Knockdown of Notch Ligands in Primary CD4 T Cells and Dendritic Cells Enhances Cytokine Production," The Journal of Immunology, 177: 885-895 (2006).

Stupp et al., "Radiotherapy plus concomitant and adjuvant temozolomide for glioblastoma," N. Engl. J. Med., 352(10): 987-996 (2005).

Vaickus et al., "Immune markers in hematologic malignancies," Crit. Rev. Oncol. Hematol., 11(4): 267-297 (1991).

Wang et al., "Notch Promotes Radioresistance of Glioma Stem Cells," Stem Cells, 28(1): 17-28 (2010).

Wu et al., "Therapeutic antibody targeting of individual Notch receptors," Nature, 464(7291): 1052-1057.

International Search Report as issued in PCT/US10/56199 on Jan. 11, 2011.

\* cited by examiner

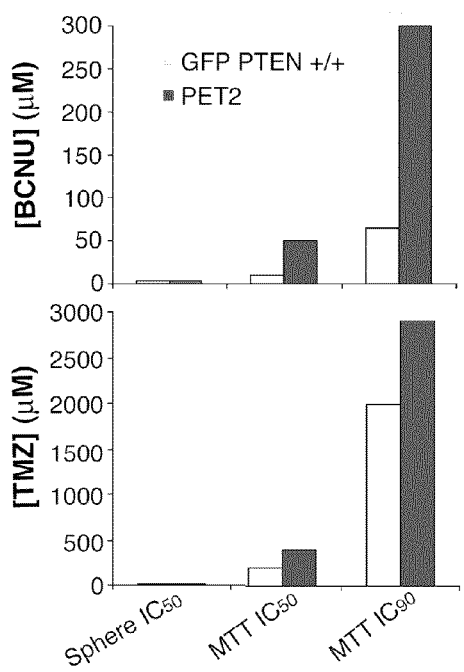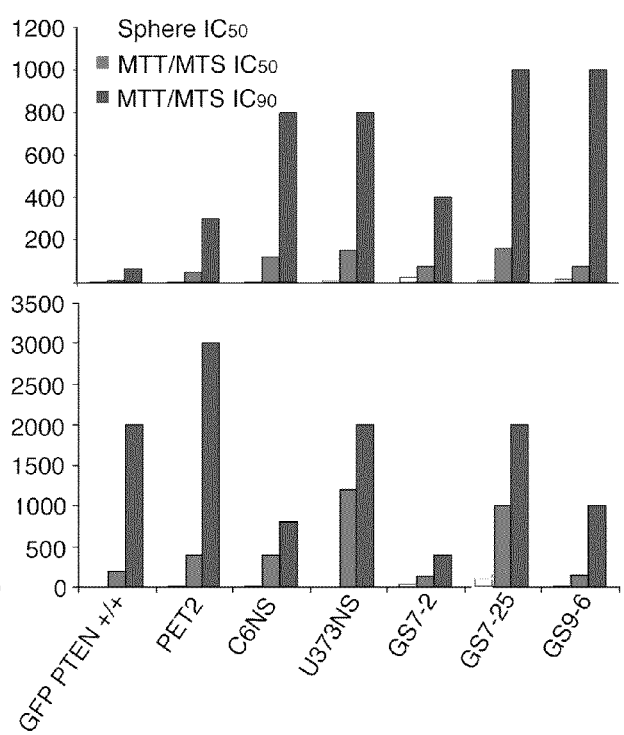
FIG. 2A
FIG. 2C
FIG. 2B
FIG. 2D

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetically generated oligonucleotides (PCR
      primers)

<400> SEQUENCE: 1
ctaaactccc caacccacct                                                   20

<210> SEQ ID NO 2
<211> LENGTH: 25
<212> TYPE: DNA
<213> ORGANISM: Artificial Sequence
<220> FEATURE:
<223> OTHER INFORMATION: Synthetically generated oligonucleotides (PCR
      primers)

<400> SEQUENCE: 2
aaggcgcaat ccaatatgaa catat                                             25

<210> SEQ ID NO 3
<211> LENGTH: 17
<212> TYPE: DNA
<213> ORGANISM: Artificial Sequence
<220> FEATURE:
<223> OTHER INFORMATION: Synthetically generated oligonucleotides (PCR
      primers)

<400> SEQUENCE: 3
gctcgtcgac aacggct                                                      17
```

```
<210> SEQ ID NO 4
<211> LENGTH: 25
<212> TYPE: DNA
<213> ORGANISM: Artificial Sequence
<220> FEATURE:
<223> OTHER INFORMATION: Synthetically generated oligonucleotides (PCR
      primers)

<400> SEQUENCE: 4
caaacatgat ctgggtcatc ttctc                                          25

<210> SEQ ID NO 5
<211> LENGTH: 22
<212> TYPE: DNA
<213> ORGANISM: Artificial Sequence
<220> FEATURE:
<223> OTHER INFORMATION: Synthetically generated oligonucleotides (PCR
      primers)

<400> SEQUENCE: 5
ttgccgacag gatgcagaag ga                                             22

<210> SEQ ID NO 6
<211> LENGTH: 22
<212> TYPE: DNA
<213> ORGANISM: Artificial Sequence
<220> FEATURE:
<223> OTHER INFORMATION: Synthetically generated oligonucleotides (PCR
      primers)

<400> SEQUENCE: 6
aggtggacag cgaggccagg at                                             22
```

METHODS FOR TREATING GLIOBLASTOMA

CLAIM OF PRIORITY

This application claims the benefit of U.S. Provisional Patent Application Ser. No. 61/260,487, filed on Nov. 12, 2009, the entire contents of which are hereby incorporated by reference.

FEDERALLY SPONSORED RESEARCH OR DEVELOPMENT

This invention was made with Government support under Grant No. RO1 NS021716, awarded by the National Institutes of Health. The Government has certain rights in the invention.

TECHNICAL FIELD

This invention relates to methods for treating cancers, e.g., glioblastoma, including administering an inhibitor of Notch signalling, e.g., a gamma secretase inhibitor, in combination with a chemotherapeutic agent.

BACKGROUND

Glioblastoma multiforme (GBM) is the most aggressive class of brain tumors, making up 17% of all primary brain tumors in the United States, with an incidence of 3.17 cases per 100,000 persons/year (CBTRUS. CBTRUS Statistical Report: Primary Brain and Central Nervous System Tumors Diagnosed in the United States in 2004-2006, Hinsdale, IL: Central Brain Tumor Registry of the United States; 2010). Although they generally do not metastasize out of the brain, they do spread aggressively through normal brain tissue. The current five- and ten-year survival rates for GBM patients are 4,5% and 2.7%, respectively (Id.).

The current treatment for GBMs is an intense combination of surgical resection or debulking, radiotherapy and chemotherapy. The most effective chemotherapy drug is temozolomide (TMZ, also known as TEMODAR™), which is an alkylating agent that is taken orally and readily penetrates the blood-brain barrier (Ostermann et al., Clin Cancer Res 2004; 10: 3728-36). This aggressive treatment increases the two-year survival rate for GBM patients from 10.4% with radiotherapy alone, to 26.5% (Stupp et al., N Engl J Med 2005; 352: 987-96). Cells that escape radiotherapy- and chemotherapy-induced cell death eventually re-enter the cell cycle and contribute to local tumor recurrence. Despite advances in chemotherapy regimens, the median progression-free survival, which measures the time until tumor recurrence, is 6.9 months, and the median overall survival is 14.6 months with temozolomide and radiotherapy (Stupp et al., N Engl J Med 2005; 352: 987-96). Hence, there is a dire need to target the cells that evade current treatments.

SUMMARY

The present invention is based, at least in part, on the discovery that the administration of a Notch inhibitor, e.g., a gamma secretase inhibitor, in combination with a chemotherapeutic agent that induces cell quiescence, e.g., alkylating agent, e.g., temozolomide (TMZ), greatly increases cell senescence in a model of GBM. Thus, the present invention includes methods for the treatment of subjects who have cancer, e.g., GBM, comprising administering a therapeutically effective amount of a Notch inhibitor, e.g., a gamma secretase inhibitor (GSI), in combination with a therapeutically effective amount of a chemotherapeutic agent, e.g., an alkylating agent, e.g., temozolomide (TMZ). These studies indicate that following treatment with TMZ some tumor cells become quiescent, whereas TMZ in combination with the GSI induces senescence.

Thus, in one aspect, the invention provides methods for treating a cellular proliferative disorder in a subject. The methods include selecting a subject who is in need of treatment for a cellular proliferative disorder, e.g., cancer, e.g., cancer associated with cancer stem cells, e.g., neural cancer, brain cancer, leukemia, breast cancer, or prostate cancer); administering to the subject a therapeutically effective amount of a chemotherapeutic agent (e.g., an alkylating agent, an agent that induces cell quiescence, and/or an agent that targets O6-guanine); and administering to the subject a therapeutically effective amount of a gamma secretase inhibitor, thereby treating the cellular proliferative disorder in the subject.

In some embodiments, the cellular proliferative disorder is glioblastoma.

In some embodiments, the chemotherapeutic agent is an alkylating agent, e.g., temozolomide (TMZ) or BCNU.

In some embodiments, the gamma secretase inhibitor is selected from the group consisting of semagacestat ((2S)-2-Hydroxy-3-methyl-N-[(1S)-1-methyl-2-oxo-2-[[(1S)-2,3,4,5-tetrahydro-3-methyl-2-oxo-1H-3-benzazepin-1-yl]amino] ethyl]butanamide, also known as LY450139; Eli Lilly and Co.), Compound E ([(2S)-2-{[(3,5-Difluorophenyl)acetyl] amino}-N-[(3S)-1-methyl-2-oxo-5-phenyl-2,3-dihydro-1H-1,4-benzodiazepin-3-yl]propanamide], available from Alexis Biochemicals), LY411575 (Eli Lilly and Co.), L-685,458 (Sigma-Aldrich), BMS-289948 (4-chloro-N-(2,5-difluorophenyl)-N-((1R)-{4-fluoro-2-[3-(1H-imidazol-1-yl)propyl]phenyl}ethyl)benzenesulfonamide hydrochloride) and BMS-299897 (4-[2-((1R)-1-{[(4-chlorophenyl)sulfonyl]-2,5-difluoroanilino}ethyl)-5-fluorophenyl]butanoic acid) (Bristol Myers Squibb), MK0752 (Merck), and MRK-003 (Merck).

In some embodiments, the gamma secretase inhibitor is administered after the chemotherapeutic agent, e.g., at least 24 hours after the chemotherapeutic agent.

In some embodiments, the methods include administering two or more doses of is the chemotherapeutic agent, and/or two or more doses of the gamma secretase inhibitor.

In another aspect, the invention provides kits including one or more doses of a chemotherapeutic agent, and one or more doses of a gamma secretase inhibitor, and instructions for administration of the chemotherapeutic agent and the gamma secretase inhibitor.

In some embodiments, the kit includes one or more doses of TMZ, and one or more doses of a gamma secretase inhibitor selected from the group consisting of semagacestat (LY450139; Eli Lilly and Co.), LY411575 (Eli Lilly and Co.), Compound E, L-685,458 (Sigma-Aldrich), BMS-299897 (Bristol Myers Squibb), MK0752 (Merck), and MRK-003 (Merck).

As used herein, "quiescence" is defined as cell cycle arrest in G1 or C0. There are no known specific markers for quiescence. Quiescence is generally reversible.

As used herein, "senescence" is defines as permanent cell cycle arrest; it is generally induced by high passage number or stress-induced damage caused by radiation or chemotherapy. Senescent cells are usually arrested in G1, though some types arrest in G1 and G2/M. β-galactosidase staining due to expanded lysosomal compartment can be used as a marker of senescence. Other markers of senescence include the cell cycle blockers p21 and/or p16.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2A-2D are bar graphs showing the effects of BCNU (2A and 2C) or TMZ (2B and 2D) treatment on various kinds of cells. The cultures were monitored by counting the number of neurospheres and a MTT or MTS assay to assess total cell number. Neurosphere numbers are an indication of clonogenicity and self-renewal.

DETAILED DESCRIPTION

Figure 1:
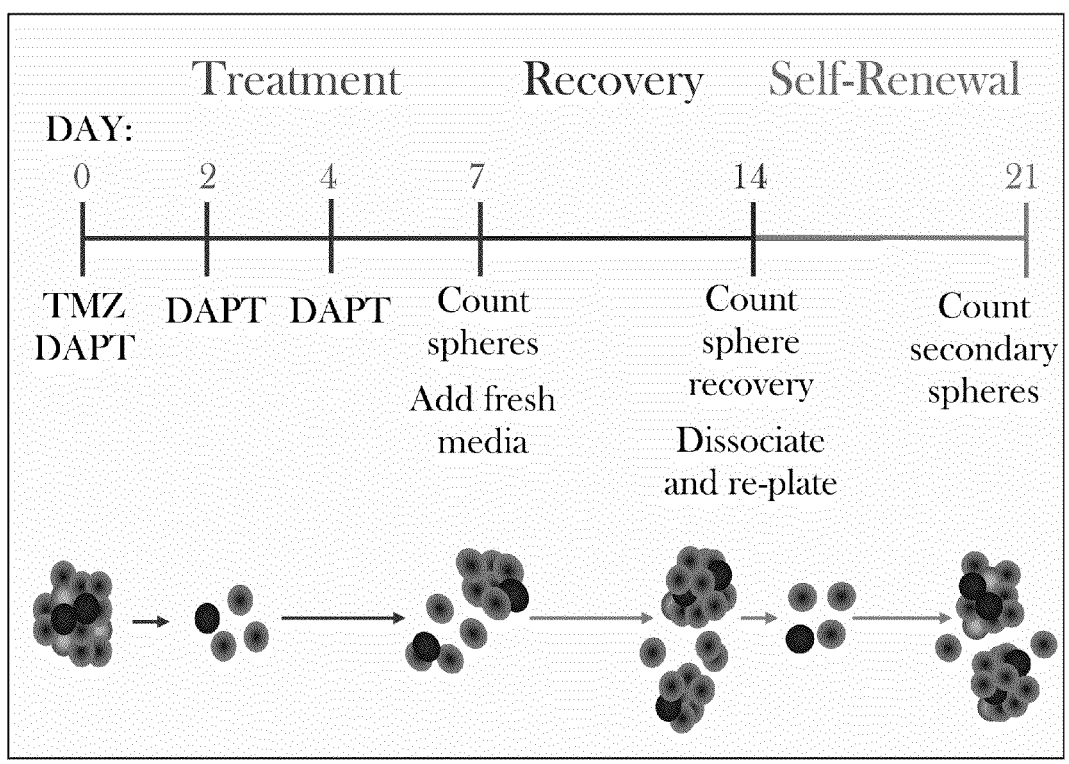
FIG. 1 is a schematic illustration of an experimental protocol described herein.

GBMs and other cancers chiding leukemias, breast cancer, prostate cancer) are believed to include a small population of cancer stem cells (CSCs) that are resistant to current therapies; in vitro, these CSCs form neurospheres in serum-free media (see, e.g., Reynolds and Weiss Dev. Biol. 175, 1-13 (1996)). As described herein, chemotherapy treatment drastically decreased sphere formation GBM cultures. However, a small number of cells entered into a reversible quiescent state and formed spheres after a short recovery period. These results suggest that treatments might be more efficient if they directly target the CSCs. One such target is the Notch pathway, which is active in normal neural stem cells and overexpressed in brain tumors. As one hypothesis, treatment with chemotherapy plus inhibition of the Notch pathway with gamma-secretase inhibitors (GSIs) targets a CSC population; the combination is a more effective therapy against GBMs and other cancers associated with CSCs than chemotherapy alone. As described herein, treatment with TMZ+DAPT (a GSI) inhibits both initial sphere formation and recovery of sphere formation in subsequent weeks. Cultures treated with TMZ+DAPT have an increase in senescence compared to TMZ-only. Treating the cultures ex vivo with TMZ+DAPT greatly reduced tumor formation in a mouse subcutaneous xenograft model, while TMZ-only ex vivo treatment only delayed tumor formation. Thus, inhibiting the Notch pathway in combination with chemotherapy enhances GBM treatment, possibly by targeting the chemoresistant CSC population.

Recent studies in several laboratories (see, e.g., Lee et al., Cancer Cell 9:391-403 (2006); Foroni et al., Cancer Res 67:3725-3733 (2007)) have demonstrated that GBM cultures in defined medium provide a better model than classical cell lines maintained with fetal bovine serum. In the present experiments, a series of brain tumors were placed into culture. We used these cultures to test the hypothesis that cancer stem cells (CSC) are relatively resistant to chemotherapy, using neurosphere formation as an assay for CSCs. To our surprise, the concentrations of chemotherapy drugs required to inhibit neurosphere formation are much lower than those required to inhibit bulk cell proliferation or to induce cell death. Further study demonstrated that inhibition of neurosphere formation is due to reversible quiescence of CSCs, which facilitates DNA repair, lessens chemotoxicity and hence, decreases the efficacy of chemotherapy.

Methods of Treatment

The methods described herein include methods for the treatment of disorders associated with abnormal apoptotic or differentiative processes, e.g., cellular proliferative disorders or cellular differentiative disorders, e.g., cancer. In some embodiments, the disorder is glioblastoma. Generally, the methods include administering a therapeutically effective amount of a combination of a GSI and a chemotherapeutic agent, e.g., an alkylating agent (e.g., mechlorethamine, thioepa chlorambucil, CC-1065, melphalan, carmustine (BSNU) and lomustine (CCNU), cyclophosphamide, busulfan, TMZ, dibromomannitol, streptozotocin, mitomycin C, and cis-dichlorodiamine platinum (II) (DDP) cisplatin), to a subject who is in need of, or who has been determined to be in need of, such treatment. In some embodiments, the chemotherapeutic agent is TMZ. In some embodiments, the GSI is LY450139.

As used in this context, to "treat" means to ameliorate at least one symptom of the disorder. In some embodiments, a treatment can result in a reduction in tumor size or number, or a reduction in tumor growth or growth rate.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and origin.

As used herein, the terms "cancer", "hyperproliferative" and "neoplastic" refer to cells having the capacity for autonomous growth, i,e., an abnormal state or condition characterized by rapidly proliferating cell growth. Hyperproliferative and neoptastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, e.g., affecting the nervous system, lung, breast, thyroid, lymphoid, gastrointestinal, and genito-urinary tract, as well as adenocarcinomas, which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Glioblastoma Multiforme (GBM)

In some embodiments, the proliferative disorder is glioblastoma multiforme (GBM). According to the WHO classification of the tumors of the central nervous system, GBM is an astrocytic tumor that includes giant cell glioblastoma and gliosarcoma. An initial diagnosis of GBM is generally made using CT or MRI, in which the glioblastomas generally appear as ring-enhancing lesions. Confirmation of the diagnosis is made based on a biopsy, e.g., a stereotactic biopsy or a craniotomy with tumor resection.

Pharmaceutical Compositions and Methods of Administration

The methods described herein include the manufacture and use of pharmaceutical compositions comprising GSIs as active ingredients. Also included are pharmaceutical compositions comprising GSIs plus chemotherapeutic agents, e.g., agents for treating GBM, e.g., TMZ or other alkylating agents, e.g., mechlorethamine, thioepa chlorambucil, CC-1065, melphalan, carmustine (BCNU) and lomustine (CCNU), cyclophosphamide, busulfan, dibromomannitol, streptozotocin, mitomycin C, and cis-dichlorodiamine platinum (II) (DDP) cisplatin.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., agents known in the art for treating cancer, e.g., chemotherapeutic agents for treating GBM, e.g., TMZ.

Pharmaceutical compositions are typically formulated to be compatible with its intended route of administration. Examples of routes of administration include parenteral, e.g., intravenous, intradermal, subcutaneous, oral (e. inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheytene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyarthydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Gamma Secretase Inhibitors (GSIs)/Notch Inhibitors

A number of gamma secretase inhibitors are known in the art (e.g., arylsulfonamides (AS), dibenzazepines (DBZ), benzodiazepines (BZ), N-[N-(3,5-difluorophenacetyl)-L-alanyl]-(S)-phenylglycine t-butyl ester (DAPT), [(2S)-2-{[(3,5-Difluorophenyl)acetyl]amino}-N-[(3S)-1-methyl-2-oxo-5-phenyl-2,3-dihydro-1H-1,4-benzodiazepin-3-yl] propanamide] (Compound E), semagacestat (LY450139; Eli Lilly and Co.), N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-L-alaninamide (LY411,575) (Fauq et al., Bioorg Med Chem Lett 2007; 17: 6392-5) (Eli Lilly and Co.), L-685,458 (Sigma-Aldrich), BMS-299897 (Bristol Myers Squibb), MK0752 (Merck), and MRK-003 (Merck). These and other agents are described in Rizzo et al., Oncogene 27:5124-5131 (2008); Olson and Albright, Current Topics Medicinal Medicine 8:17-33 (2008); Graziani et al., Cancer Res. 68:9678-9685 (2008); Rao et al., Cancer Res. 69:3060-3068 (2009); Sharma et al., Mol. Cell. Biol. 26:8022-8031 (2006); Cullion et al., Blood. 113:6172-6181 (2009); Cho et al., J. Immunol. 182:3380-3389 (2009); Samon et al., Blood 112:1813-1821 (2009); Joshi et al., Blood 113:1689-1698 (2009); Fleisher et al., Arch. Neurol. 65:1031-1038 (2009); Lanz et al., J. Pharmacol. Exp. Therapeutics 319:924-933 (2006); Spilman et al., PNAS 105: 10595-10600 (2008); and Namihira et al., Dev Cell 16:245-255 (2009).

Alternatively or in addition, other inhibitors of Notch signaling can be used. Other Notch inhibitors include anti-Notch antibodies and antigen-binding fragments thereof, as well as inhibitory nucleic acids (e.g., small interfering RNAs, antisense oligonucleotides, and morpholino oligos); methods for designing, making, and using them are known in the art, e.g., gene walk methods for selecting and optimizing inhibitory sequences, see, e.g., Engelke, RNA Interference (RNAi): The Nuts & Bolts of siRNA Technology, (DNA Press, 2004); Mol, Antisense Nucleic Acids and Proteins, (CRC, 1994); Sioud, Ribozymes and Sima Protocols (Methods in Molecular Biology), (Humana Press; 2nd edition 2004); and Philips, Antisense Therapeutics (Methods in Molecular Medicine), (Humana Press 2004)) targeting Notch (see, e.g., Presente et al., Proc. Nat. Acad. Sci. 101(6):1764-1768 (2004); Ivanov et al., Proc. Nat. Acad. Sci. 101(46):16216-16221 (2004)) or its ligands, i.e., Delta or Jagged (see, e.g., Patzel et al., Nature Biotechnology 23, 1440-1444 (2005); Purow et al., Cancer Research 65:2353-2363 (2005); or Stallwood et al., J. Immunol. 177:885-895 (2006)). Alternatively, the cells can be modified to express m-Numb (GenBank Acc. No. NP_001005743.1) or disheveled (Dvl; the human homologs are at GenBank Acc. No. NM_004421.2 (variant 1); NM_004422.2 (variant 2); and NM_004423.3 (variant 3), both endogenous inhibitors of Notch signalling.

Chemotherapeutic Agents

In some embodiments, the methods include the administration of a GSI and one or more chemotherapeutic agents for treating cancer, e.g., GBM, e.g., TMZ (temozolamide, sold under the trade name TEMODAR™ (Schering-Plough)). Other chemotherapeutic agents can also be used in addition or in alternative to TMZ, e.g., one or more of: Accutane (Hoffmann-La Roche); AEE788 (Novartis); AMG-102; Anti Neoplaston; AQ4N (Banoxantrone); AVANDIA (Rosiglitazone Maleate); Avastin (Bevacizumab) Genetech; 1,3-Bis(2-chloroethyl)-1-nitrosourea (BCNU) (Carmustine); Carboplatin; CCI-779; CCNU Lomustine; Celecoxib (Systemic); Chloroquine; Cilengitide (EMD 121974); Cisplatin; CPT-11 (CAMPTOSAR, Irinotecan); Dasatinib (BMS-354825, Sprycel); Dendritic Cell Therapy; Etoposide (Eposin, Etopophos, Vepesid); Gleevec (imatinib mesylate); GLIADEL Wafer; Hydroxyurea; IL-13; Immune Therapy; Iressa (ZD-1839); Lapatinib (GW572016); Methotrexate for Cancer (Systemic); OSI-774; PCV; Procarbazine; RAD001 Novartis (mTOR inhibitor); Rapamycin (Rapamune, Sirolimus); RMP-7; RTA 744; Simvastatin; Sirolimus; Sorafenib; SU-101; SU5416 Sugen; Sulfasalazine (Azulfidine); Tamoxifen; TARCEVA (erlotinib HCl); TGF-B Anti-Sense; Thalomid (thalidomide); VEGF-Trap; Vincristine; Vorinostat (SAHA); XL184; XL765; Zamestra (tipifarnib); ZOCOR (simvastatin). In some embodiments, the agent is an alkylating agent (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and/or cis-dichlorodiamine platinum (II) (DDP) cisplatin. In some embodiments, the agent targets O6-guanine, e.g., TMZ or BCNU. In embodiments in which the tumor is in the brain, e.g., glioblastoma, it is desirable to select a chemotherapeutic agent that enters the brain, e.g., that can readily cross the blood-brain barrier. The agent can be administered using methods known in the art as appropriate for that agent. For example, TMZ is administered orally. In some embodiments, e.g., where the agent is 1,3-Bis (2-chloroethyl)-1-nitrosourea (BCNU), the agent can be surgically implanted in a wafer in the brain (slowly dissolving BCNU wafers are commercially available under the trade name GLIADEL, from Eisai Pharmaceuticals). Although the GLIADEL wafers are an appealing method for administration, BCNU can also be administered intravenously.

Dosage

An "effective amount" is an amount sufficient to effect beneficial or desired results. For example, a therapeutic amount is one that achieves the desired therapeutic effect, e.g., cell senescence/cell death, tumor shrinkage. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Example 1

Chemotherapy Treatment Alone is Insufficient

Glioblastoma multiforme (GBM) patients undergo an intense combination of surgery, radiation and chemotherapy, usually with temozolomide (TMZ) or 1,3-Bis(2-chloroethyl)-1-nitrosourea (BCNU) (which is an older alkylating agent that TMZ has replaced), but these treatments are only palliative. GBMs are believed to include a small population of cancer stem cells (CSCs) that are resistant to current therapies; as shown herein, these cells can be cultured in defined medium and form neurospheres in serum-free media.

Methods for culturing neural stem cells are described, e.g., in Reynolds and Weiss, Dev. Biol. 175:1-13 (1996). The subventricular zone (SVZ) and dentate gyrus have the highest numbers of neural stem cells in adult brains. SVZ cells can be obtained from embryos or adult mice, and cultured using defined medium (DMEM/F12 medium with supplement B27) with 20 ng/ml bFGF and 20 ng/ml epidermal growth factor (EGF). The cells form neurospheres, growing as large, nonadherent clusters of cells. These cells express the neural stem cell marker, nestin. GBM cultures have traditionally used 10% fetal bovine serum, but as shown herein GBM cells can be grown as neurospheres defined stem cell medium with EGF+FGF (20 ng/ml of each). When grown as neurospheres, the GBM cells express stem cell markers, and addition of serum induces differentiation to astrocytic cells. In contrast to serum cultures, the neurosphere cells are invasive when injected into brains of immunodeficient mice (Lee et al., Cancer Cell 9, 391-403 (2006)). The gene expression profile of GBM cells grown in sphere cultures is a better match for the original tumors than GBM cells grown in serum.

Two human fetal bovine serum-dependent GBM cell lines (U373MG and U87MG) and one rat line (C6) were converted to sphere growth in defined medium with EGF+FGF (20 ng/ml of each). Additional cell lines were prepared using cells from excised tissue.

The effect of chemotherapy on neurosphere formation was assayed in glioma neurosphere cultures. A schematic illustration of the experimental protocol is shown in FIG. 1. Cultures are treated with a single dose of the agent, e.g., TMZ and multiple doses of a GSI, e.g., DAPT to inhibit the Notch pathway. After the Treatment phase, the number of initial spheres (counted about 7 days after TMZ treatment) represents the number of proliferating CSC/progenitors (FIG. 1 for schematic). Recovery (counted 14 days after TMZ treatment) includes enlargement of the initial spheres and new spheres formed when CSC/progenitor cells quiescent as a result of chemotherapy resume cell proliferation. Secondary sphere formation is a demonstration that the CSC/progenitor cells following treatment with chemotherapy drugs are still capable of self-renewal of neurospheres, i.e., cells from neurospheres are tested to see if they can form new neurospheres. The cells used included U87NS, a neurosphere culture converted to neurosphere growth in defined medium from U87MG (an old Swedish line that is grown in conventional serum conditions); GS7-2, GS8-26 and GS6-22 primary neurosphere cultures that were obtained from grade IV GBM patient tumor samples and AS5-15, which was obtained from a grade III anaplastic astrocytoma.

TMZ (obtained from Sigma-Aldrich (St. Louis, Mo.)) treatment at 100-200 uM greatly decreases the formation of neurospheres and cell viability in both wild type NSCs and GBM tumor-derived cells. The sphere IC50 (the concentration of drug that inhibits neurosphere formation by 50%), bulk IC50 (concentration of drug that reduces bulk or total cells by 50%), and bulk IC90 (concentration of drug that reduces bulk or total cells by 90%; at this concentration, there is always cell toxicity) for TMZ and BCNU were determined for several of the cell lines, and compared to the in vivo effective doses. The concentration of TMZ in the cerebral spinal fluid (about 5 μM) is similar to the dose required for inhibition of neurosphere formation and much less than that required for cytotoxicity (see FIGS. 2A-D). In vivo, BCNU is commonly administered by surgeons, leaving slowly dissolving BCNU wafers (GLIADEL, Eisai Pharmaceuticals) in the tumor bed. Near the GLIADEL wafers, the BCNU is estimated to reach high concentrations (about 1 mM), which is much higher than the neurosphere-inhibitory dose and the cytotoxic dose in vitro (see FIGS. 2B and 2D). In addition, there was an increase in neurosphere number after a recovery period following treatment with either TMZ or BCNU; this indicates the presence of a subpopulation of cells that survived the chemotherapy treatment, likely by entering a reversible cell arrest.

These results demonstrate that chemotherapy treatment drastically decreased sphere formation, particularly in O-6-Methylguanine-DNA Methyltransferase (MGMT)-negative cultures. MGMT is a key determinant for sensitivity to TMZ; it reverses the modification of DNA by TMZ, so that tumor cells that express MGMT are less sensitive to TMZ. However, patients with MGMT-positive tumors are often still treated with TMZ because there is no effective alternative. In addition, TMZ-treated tumors are capable of re-growth. These results suggest that a small number of cells enter into a reversible quiescent state, and form spheres or re-grow after a short recovery period; thus, treatments would likely be more efficient if they directly target the CSCs.

Example 2

Glioma Neurosphere Cell Lines Express Notch Receptors and Downstream Targets

One potential method of targeting CSCs is via the Notch pathway which is active in normal neural stem cells and over-expressed in brain tumors. Hes1, a downstream Notch target, controls the reversibility of quiescence (Sang et al., Science 321:1095-1100 (2008)). Inactivation of Hes1 switches senescent fibroblasts into an irreversible senescent state, and inhibiting the Notch pathway depletes CSCs medulloblastoma (Fan et al., Cancer Res 66, 7445-7452 (2006).

To determine whether these pathways are active in glioma, glioma cell lines converted to neurosphere cultures, U87NS and U373NS, and primary GBM lines, GS7-2 and GS8-26, were grown in serum-free defined medium consisting of DMEM/F12 1:1 (GIBCO, Carlsbad, Calif.), B27 (GIBCO, Carlsbad, Calif.), 15 mM HEPES (GIBCO, Carlsbad, Calif.), 20 ng/ml EGF (Invitrogen, Carlsbad, Calif.), and 20 ng/ml bFGF (Invitrogen, Carlsbad, Calif.) and 1% penicillin-streptomycin (GIBCO, Carlsbad, Calif.). Cultures were passaged using a dissociation method (Sen et al., Tissue Eng 2004; 10: 904-13). Details of the converted and primary lines were as follows.

U373MG (Dr. Larry Recht, Stanford University) and U87MG (ATCC) were grown in DMEM (GIBCO, Carlsbad, Calif.) with 10% FBS (Sigma-Aldrich, St. Louis, Mo.). To convert the U87MG adherent serum culture into the U87NS neurosphere culture, cells were trypsinized and immediately plated in serum-free, defined medium consisting of DMEM/F12 1:1 (GIBCO, Carlsbad, Calif.), B27 (GIBCO, Carlsbad, Calif.), 15 mM HEPES (GIBCO, Carlsbad, Calif.), 20 ng/ml EGF (Invitrogen, Carlsbad, Calif.), and 20 ng/ml bFGF (Invitrogen, Carlsbad, Calif.) and 1% penicillin-streptomycin (GIBCO, Carlsbad, Calif.). To convert the U373MG adherent serum culture into the U373NS neurosphere culture, cells were propagated in DMEM/F12 1:1 (GIBCO, Carlsbad, Calif.) containing 20% FBS until confluent and adherent neurospheres formed. The media was then switched to serum-free, defined media and the cells grew as suspension neurospheres.

TMZ concentrations for each culture were selected based on previous experiments (Mihaliak et al., Cancer Letts. 296, 168-177 (2010)) DAPT and LY concentrations were chosen for each culture based on the decrease in Hes1 and Hey1 expression. RNA was isolated from the cultures 48 hours after DAPT treatment, and Hes1 and Hey1 cDNA expression levels were analyzed by PCR or qPCR.

The University of Massachusetts Medical School Tissue Bank supplied resected brain tumor tissue for GS8-26 after surgery. All procedures had Institutional Review Board approval. Tumor tissue was cut into small sections and incubated at 37° C. in a 1:1 mixture of defined medium and crude trypsin. The tissue was triturated every 10 minutes to obtain single cell suspensions. After one hour, the cells were washed with PBS and plated in defined medium. The first neurospheres formed within two to three weeks. We classify primary cultures from grade IV GBMs. The primary neurosphere culture, GS7-2, was provided by Brent Cochran (Tufts School of Medicine) (Sherry et al., Stem Cells 2009; 27: 2383-92). All primary neurosphere experiments were completed with cultures between passages 10 and 20. Cells that express methyl guanine methyl transferase (MGMT) demonstrate an increased resistance to TMZ, because they are can repair the $O^6$-methyl-guanine lesion (Fukushima et al., Anticancer Res 2009; 29: 4845-54). Therefore, the cell cultures used in these experiments have little or no MGMT expression.

RT-PCR and RT-qPCR were performed as follows. Neurosphere cultures were pelleted and tumor tissues from subcutaneous xenografts were broken into a powder using a BioPulverizer (Biospec Products, Inc., Bartlesville, Okla.). RNA was isolated from neurosphere cultures and frozen tumor samples using TRIzol Reagent (Invitrogen, Carlsbad, Calif.), following the manufacturer's protocol. RNA was treated with DNase I, Amplification Grade (Invitrogen, Carlsbad, Calif.). cDNA was made using the SuperScript II Reverse Transcription (RT) Kit with Oligo(dT)$_{12-18}$ primers (Invitrogen, Carlsbad, Calif.), followed by a 20 minute incubation at 37° C. with RNaseH. PCR was carried out using Taq DNA Polymerase, following the manufacturer's protocol (Invitrogen, Carlsbad, Calif.). Real time qPCR was carried out using QuantiTect SYBR Green (QIAGEN, Valencia, Calif.). Hes1 and β-Actin primers were developed using Primer3 (Rozen and Skaletsky, Methods Mol Biol 2000; 132: 365-86). Hes1 forward primer: 5" CTAAACTCCCCAACCCACCT 3" (SEQ ID NO:1) and reverse primer: 5" AAGGCGCAATCCAATATGAACATAT 3" (SEQ ID NO:2). β-Actin (RT-PCR) forward primer: 5"GCTCGTCGACAACGGCT 3" (SEQ ID NO:3) and reverse primer: 5" CAAACATGATCTGGGTCATCTTCTC 3" (SEQ ID NO:4). β-Actin (qRT-PCR) forward primer: 5"TTGCCGACAGGATGCAGAAGGA 3" (SEQ ID NO:5) and reverse primer: 5" AGGTGGACAGCGAGGCCAGGAT (SEQ ID NO:6). Primers for Hey1 (Osipo et al., Oncogene 2008; 27: 5019-32), Notch1 (Lefort et al., Genes Dev 2007; 21: 562-77), Notch2 (O'Neill et al., Am J Pathol 2007; 171: 1023-36), Notch3 (Buchler et al., Ann Surg 2005; 242: 791-800, discussion -1) and Notch4 (Buchler et al., Ann Surg 2005; 242: 791-800, discussion -1) were previously published, RT-PCR products were analyzed on 2% agarose gels. tantification of band intensity for DAPT treated lines was determined using ImageJ (Rasband W S. ImageJ, U.S. National Institutes of Health, Bethesda, Md., USA. 1997-2004). cDNA levels for qRT-PCR products were calculated using the PFAFFL method (Pfaffl, Nucleic Acids Res 2001; 29: e45).

Figure 3A:
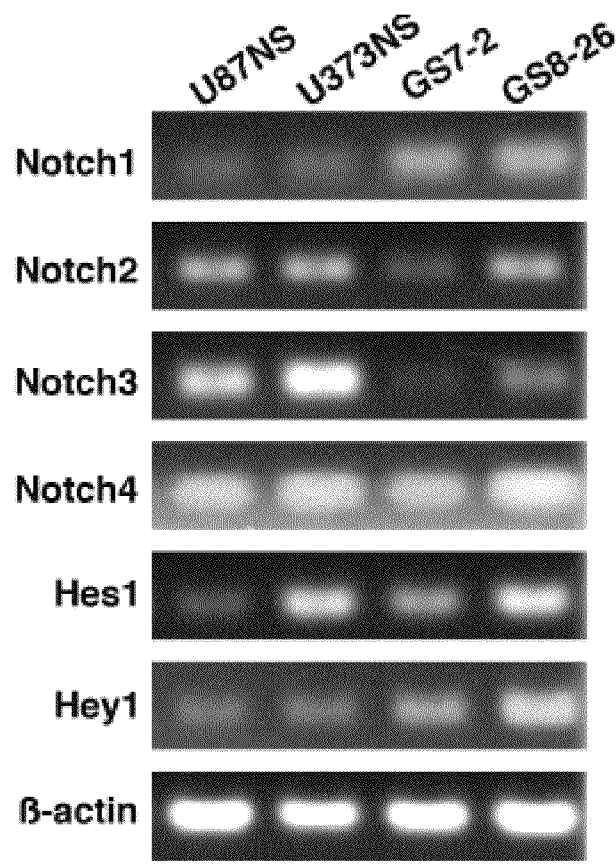
FIG. 3A is an image of an agarose gel showing mRNA levels of the Notch receptors and downstream targets measured by RT-PCR. Notch1-4, Hes1, and Hey1 were detected in each neurosphere culture. β-Actin was used for the loading control.
Figure 3B:
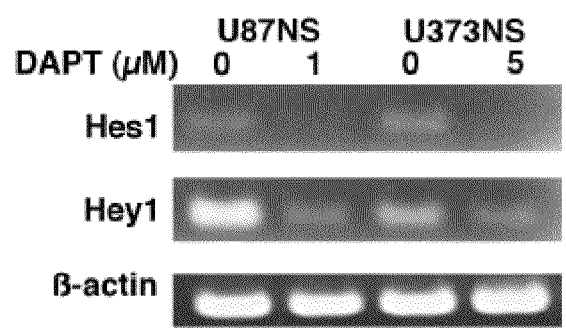
FIG. 3B is an image of an agarose gel showing Hes1, and Hey1 expression levels analyzed by RT-PCR 48 hours after DAPT treatment, DAPT treatment decreased Hes1 and Hey1 mRNA levels by 72% and 76% in U87NS (1 μM), and by 76% and 51% in U373NS (5 μM).

Converted cell lines (U87NS, U373NS) and primary neurosphere cultures established from patients "GBMs (GS7-2, GS8-26) express the mRNAs for Notch1-4 and the downstream targets, Hes1 and Hey1 (FIG. 3A). Treatment with DAPT downregulated the mRNA levels of Hes1 and Hey1 (FIG. 3B). The DAPT concentration used was determined based on a 50% or greater knockdown of Notch targets. For subsequent experiments, U87NS and GS7-2 cultures were treated with 1 μM DAPT, while U373NS and GS8-26 cultures were treated with 5 μM DAPT.

Example 3

TMZ+DAPT Treatment Inhibits Neurosphere Recovery and Secondary Neurosphere Formation To determine the effects of TMZ plus DAPT neurospheres, cells were plated as previously described (Mihaliak et al., Cancer Letts. 296, 168-177 (2010)). Immediately after plating, cells were treated with DMSO, DAPT-only, LY411,575 (LY)-only TMZ-only, TMZ+DAPT or TMZ+LY. The initial neurospheres were counted on day 7 for the converted cell lines and on day 10 for the slower growing primary lines. Neurosphere recovery was measured on day 14 or 20. The neurospheres were dissociated, re-plated and secondary neurosphere formation was measured on day 21 or 30.

Neurosphere cultures were dissociated to single cell suspensions by pH dissociation followed by filtration through 40 μm screens. For the neurosphere assay, 3,000 cells/ml of defined medium were seeded in 6-well plates. Immediately after plating, cells were treated with DMSO (Research Organics, Cleveland, Ohio) carrier control, TMZ-only, DAPT-only, or TMZ+DAPT. Additional DAPT was added on days 2 and 4. Neurospheres consisting of 10 or more cells were counted under a light microscope on day 7 for the converted cell lines. Primary lines have a slightly longer doubling time and were counted on day 10. After counting the neurospheres from the initial treatment, 2 ml of fresh defined medium was added to each well. DAPT was also added once more to the DAPT-only and TMZ+DAPT samples, and the cells were incubated for an additional 7 or 10 days. Neurospheres from the recovery period were counted on day 14 or day 20. To analyze secondary neurosphere formation, cells were collected, pelleted and dissociated to a single cell suspension by the pH method. Cells from each well were re-seeded into 6-well plates with 2 ml of defined medium. The number of secondary neurospheres formed by converted cell lines and primary cultures were counted on day 21 or day 30, respectively. All recovery assays were repeated with a minimum of 6 replicate sets of time points.

For the samples labeled "PRE-treat", a single dose of DAPT was administered when the cells were plated, and then TMZ was added to the medium 24 hours later. For the "CO-treat" samples, single doses of TMZ and DART were added simultaneously when the cells were plated. Finally, samples labeled "POST-treat" were treated with TMZ, and then DAPT was added 24 hours later.

Figure 3C:
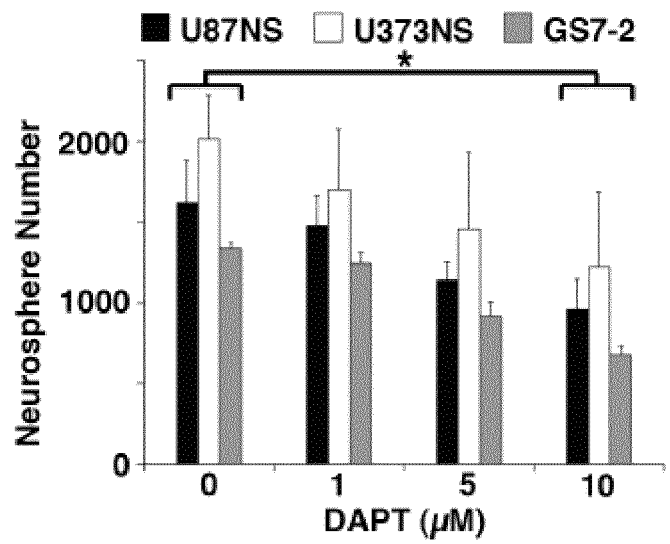
FIG. 3C is a bar graph showing the DART titration curve, demonstrating that low concentrations (1-5 μM) of DAPT-only treatment had minimal inhibition of neurosphere formation (mean±SD) in U87NS, U373NS, or GS7-2 cultures. DAPT administered at higher concentrations (10 μM) significantly decreased neurosphere formation. Neurospheres were counted on day 7 for U87NS and U373NS and on day 10 for GS7-2. The t-test was used to calculate statistical significance. *=P<0.001.
Figure 3D:
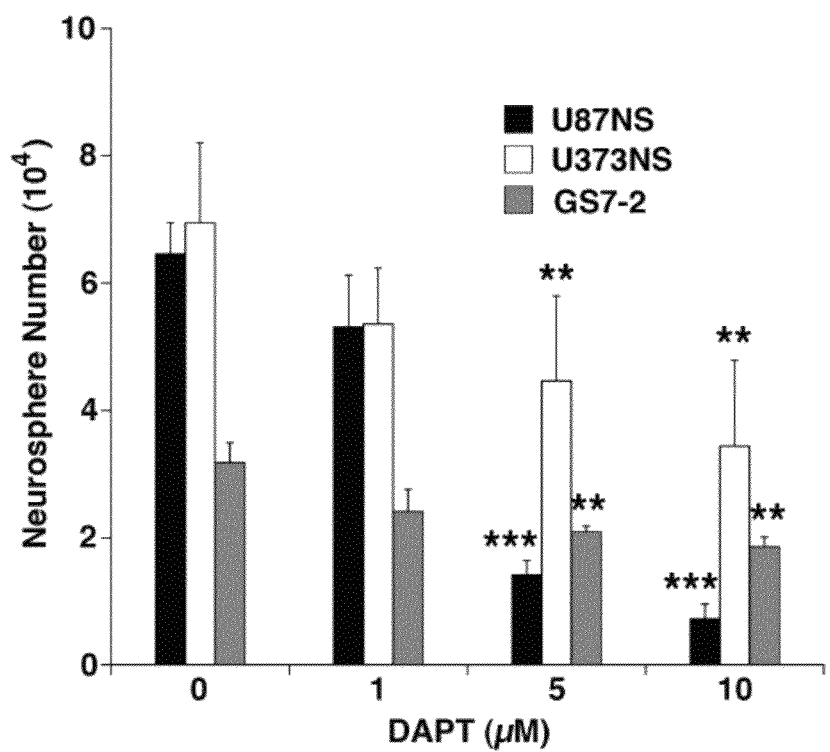
FIG. 3D is a bar graph showing secondary neurosphere formation in cells treated with varying concentrations of DAPT. U87NS, U373NS, and GS7-2 cells were treated with DMSO (0 μM DAPT) or DAPT-only at concentrations of 1, 5, and 10 μM. Neurospheres were dissociated on day 14 for U87NS and U373NS cultures or on day 20 for GS7-2 cultures and replated for secondary neurosphere formation. Despite a decrease in secondary neurosphere formation at higher concentrations of DAPT, the treated cells are capable of repopulating the culture, =P<0.01. *=P<0.001

When administered alone, low concentrations of DAPT (1-5 μM) decreased Notch pathway signaling (FIG. 3B), but had little to no affect on the number of neurospheres (FIG. 3C). In addition, low concentrations of DAPT did not affect the size of the neurospheres (FIG. 4B). In U87NS, U373NS, and GS7-2 cultures, treatment with 10 μM DAPT decreased neurosphere formation by 41%, 39%, and 49%, respectively, compared to DMSO controls (FIG. 3C); however, the DAPT treated cells resumed proliferation and formed secondary neurospheres (FIG. 3D).

Figure 4A:
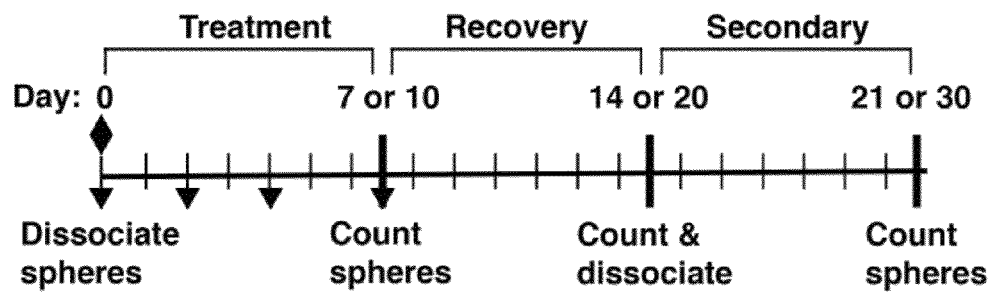
FIG. 4A is a schematic for the neurosphere recovery assay. TMZ (diamond) is administered on day 0 after cells are dissociated and plated, DAPT (inverted triangle) is administered on days 0, 2, 4, and 7.
Figure 4B:
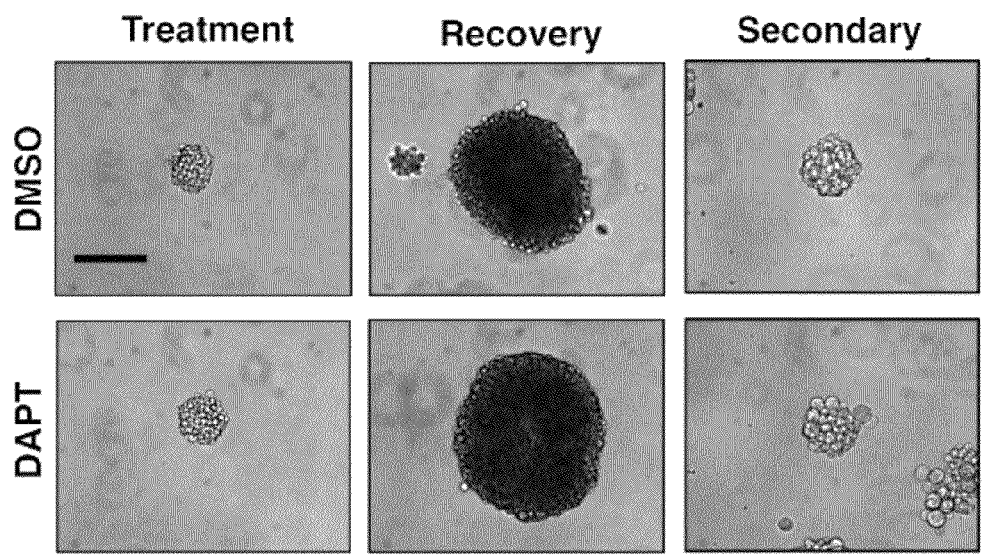
FIG. 4B is a set of six representative micrographs of U87NS neurospheres with control DMSO and DAPT (1 μM) treatments. Neurospheres treated with DAPT display a similar size compared to DMSO control cultures at treatment (day 7), recovery (day 14) and secondary (day 21) time points.
Figure 4C:
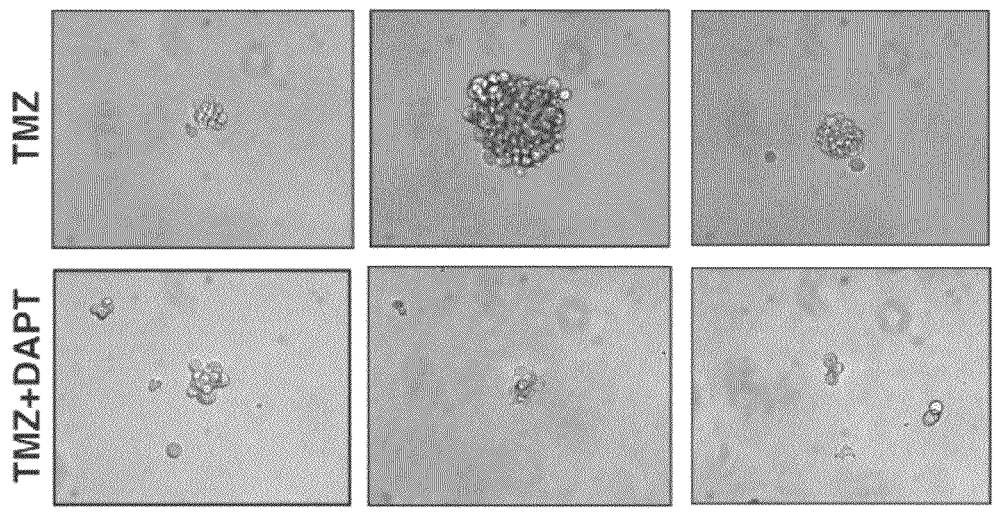
FIG. 4C is a set of six representative micrographs of U87NS neurospheres with TMZ (200 μM) treatment and TMZ (200 μM) combined with DAPT (1 μM) treatment. After the initial treatment (day 7), TMZ-only and TMZ+DAPT treated neurospheres are smaller than the control cultures. TMZ-only treated neurospheres increased in size during the recovery period (day 14) and formed secondary neurospheres (day 21), while TMZ+DAPT treated neurospheres did not increase in size or form secondary neurospheres. Bar=50 μm.
Figure 5A:
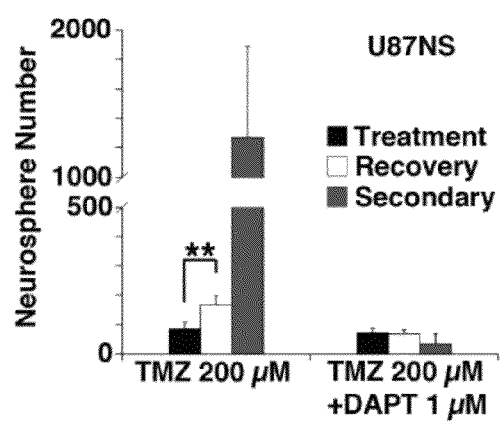
FIGS. 5A-D are bar graphs demonstrating that TMZ+DAPT treatment inhibits recovery and secondary neurosphere formation. Initial neurospheres (mean±SD) were counted on day 7 for 5A, U87NS; and 5B, U373NS cultures; or on day 10 for 5C, GS7-2, and; 5D, GS8-26 cultures. Recovery neurospheres were counted on day 14 or 20, and secondary neurospheres were counted on day 21 or 30. *=P<0.001. **=P<0.0001.
Figure 5B:
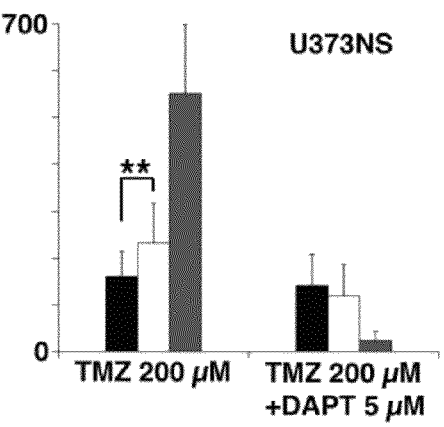
Figure 5C:
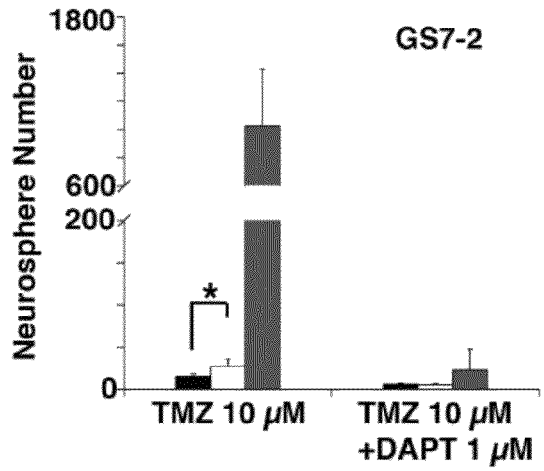

To determine if DAPT enhances TMZ therapy, we examined the effect of combined treatment on neurosphere recovery (FIG. 4A). After treatment with TMZ-only and TMZ+DAPT, cultures had similar decreases in the number of initial neurospheres formed (FIG. 4A-D). TMZ-only and TMZ+DAPT treatments decreased initial neurosphere formation by 80-98% and 83-99%, respectively. Cultures were given an additional 7 or 10 days to recover in the absence of drugs. During this recovery period, the neurospheres that formed after TMZ-only treatment increased in size; however, the TMZ+DAPT treated neurospheres remained the same size (FIG. 4C). The number of neurospheres also increased after recovery in the TMZ-only treated cultures, but this recovery was not observed in the TMZ+DAPT treated cultures. After recovery from the TMZ-only treatment, U87NS showed a 2-fold increase and U373NS showed a 1.5-fold increase in the number of neurospheres (FIGS. 5A and B). The primary neurosphere cultures also showed a recovery from the TMZ-only treatment: the number of GS7-2 neurospheres increased by 1.8-fold, and GS8-26, by 1.6-fold (FIGS. 5C and D). In contrast, TMZ+DAPT effectively inhibited recovery for U87NS, U373NS, GS7-2 and GS8-26 (FIG. 5A-D). The number of neurospheres in these cultures was essentially the same after recovery on day 14 or 20 relative to the number of initial neurospheres counted on day 7 or 10.

Figure 5D:
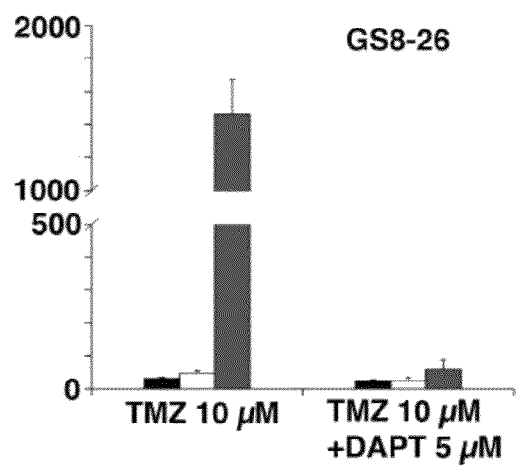

To assess if the cultures retained cells capable of self-renewal, the initial neurospheres were dissociated to single cells and re-plated to measure secondary neurosphere formation. TMZ-only treated cultures readily formed secondary neurospheres, but secondary neurosphere formation for TMZ+DAPT treated cultures was significantly diminished. U87NS secondary neurosphere formation in the TMZ-only treated culture was 36-fold greater (P<0.0001) than secondary neurosphere formation in the TMZ+DAPT treated culture (FIG. 5A), and U373NS secondary neurosphere formation in the TMZ-only treated culture was 23-fold greater (P<0.001) than in the TMZ+DAPT treated culture (FIG. 5B). The primary cultures also had profuse secondary neurosphere formation after TMZ-only treatments, but minimal secondary neurosphere formation after TMZ+DAPT treatments. Secondary neurosphere formation was 45-fold greater (P<0.001) in the GS7-2 TMZ-only treated culture (FIG. 5C) and 25-fold greater (P<0.001) in the GS8-26 TMZ-only treated culture (FIG. 5D).

The number of cells in each neurosphere capable of self-renewal can be calculated by dividing the number of secondary neurospheres by the number of neurospheres formed during the recovery period. After recovery from TMZ-only treatment, there were an average of 8 and 3 cells per neurosphere that maintained self-renewal properties in the U87NS and U373NS cultures, respectively; however, in the TMZ+DAPT treated cultures there were only approximately 0.5 cells per neurosphere that were capable of self-renewal after the recovery period. In the primary lines treated with TMZ-only, each neurosphere from the GS7-2 and GS8-26 cultures contained a large number of cells capable of self-renewal, an average of 38 and 31 cells, respectively. In contrast, the average number of cells capable of self-renewal after TMZ+DAPT treatment decreased to only 2 cells per neurosphere in the GS7-2 and GS8-26 cultures.

Figure 5E:
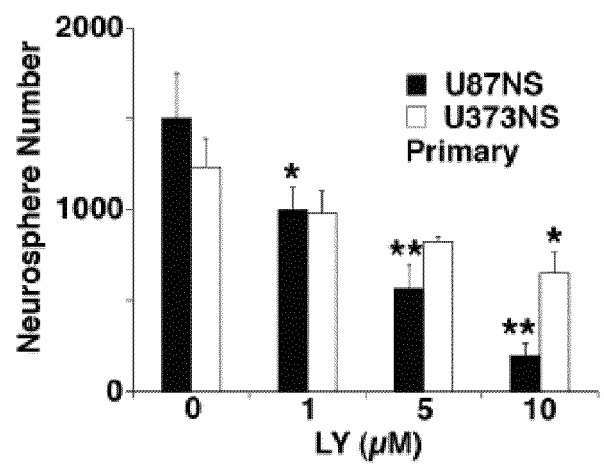
FIGS. 5E-H are bar graphs demonstrating that LY targets the Notch pathway and synergizes with TMZ treatment to inhibit neurosphere recovery. 5E, U87NS and U373NS cells were treated with varying concentrations of LY, and neurospheres were counted after 7 days. 5F, U373NS LY treated cultures have decreased secondary neurosphere formation, when compared to DMSO treated samples; however, secondary neurosphere formation was still robust. The recovery assay for 5G, U87NS and 5H, U373NS cells demonstrated that combined treatment with TMZ+LY inhibited neurosphere recovery and secondary neurosphere formation. The t-test was used to calculate statistical significance. *=P<0.05. =P<0.01 *=P<0.001.
Figure 5F:
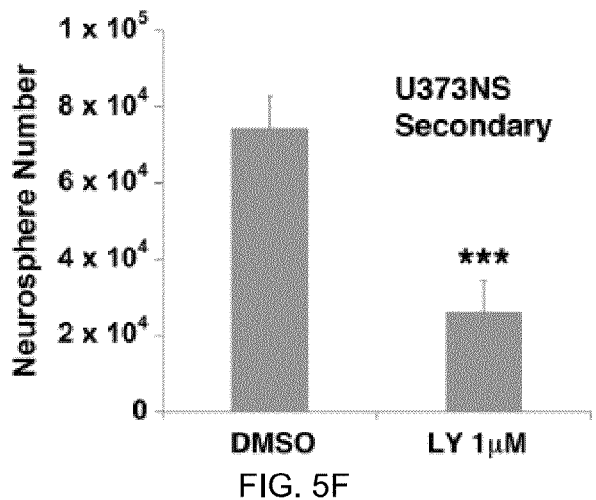
Figure 5G:
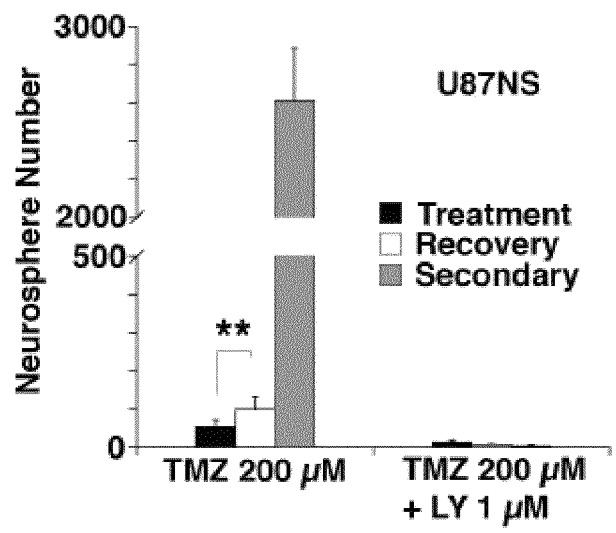
Figure 5H:
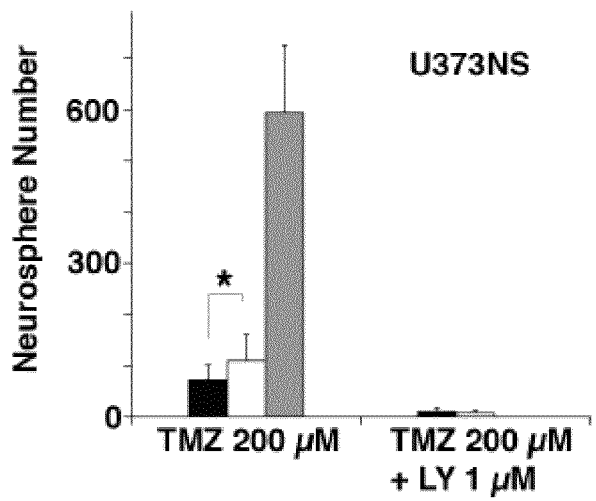

To demonstrate that the tack of recovery and secondary neurosphere formation after TMZ+DAPT treatment was a specific response to the inhibition of gamma-secretase activity, we repeated the neurosphere recovery assay with LY411,575 (LY) (Fauq et al., Bioorg Med Chem Lett 2007; 17: 6392-5). When LY was administered to U87NS and U373NS cultures at various concentrations, there was a dose-dependent decrease in neurosphere formation (FIG. 5E); however, the LY-only treated cultures retained the ability to form secondary neurospheres (FIG. 5F). In contrast, the combination of TMZ+LY significantly repressed recovery and secondary neurosphere formation (FIGS. 5G-H).

Example 4

Constitutive Expression of NICD Protects Neurosphere Cultures from TMZ+DAPT Treatment Gamma-secretase cleaves other substrates, in addition to the Notch receptors (Beel and Sanders, Cell Mol Life Sci 2008; 65: 1311-34). To establish that DAPT enhances TMZ treatment by targeting the Notch pathway, we infected U87NS and GS7-2 cells with a retrovirus to express the constitutively active Notch1 Intracellular Domain (NICD) (Pui et al., Immunity 1999; 11: 299-308).

NICD-pMIG (Pui et al., Immunity 1999; 11: 299-308) or pMIG vectors were co-transfected with retrovirus envelope and gag-pol vectors into HEK293T cells, with FuGENE 6 (Roche Applied Science, Indianapolis, Ind.). Retrovirus was collected after 48 hours. Neurosphere cultures were infected in non-coated bacterial dishes to avoid the cells becoming adherent in the presence of serum. Cells were incubated with virus and 8 µg/ml polybrene (Sigma-Aldrich, St. Louis, Mo.) at 37° C. for 6 hours. GFP-positive cells were sorted on a FACS Aria (RD Biosciences, Franklin Lakes, N.J.).

Figure 6A:
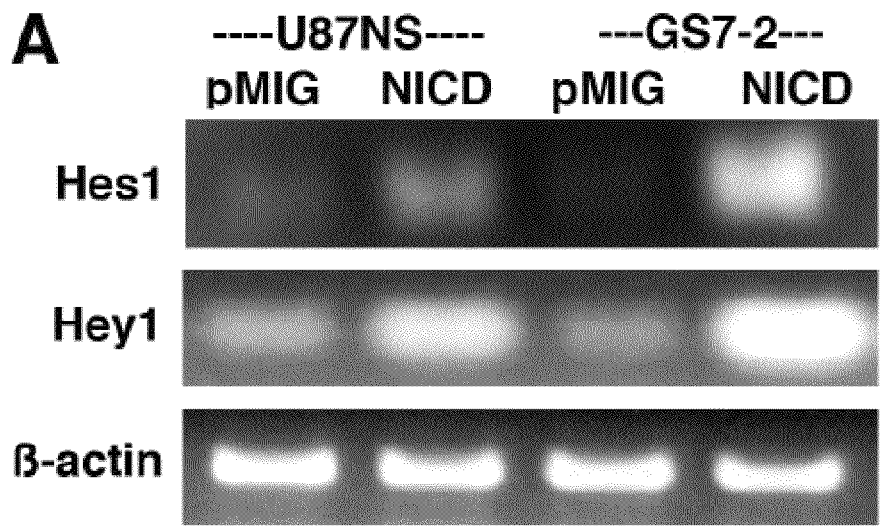
FIG. 6A is a gel showing the results of RT-PCR analysis of Hes1 and Hey1 expression was used to confirm NICD activity, Hes1 and Hey1 expression increased in U87NS-NICD and GS7-2-NICD cultures compared to cultures expressing the empty vector (pMIG).
Figure 6B:
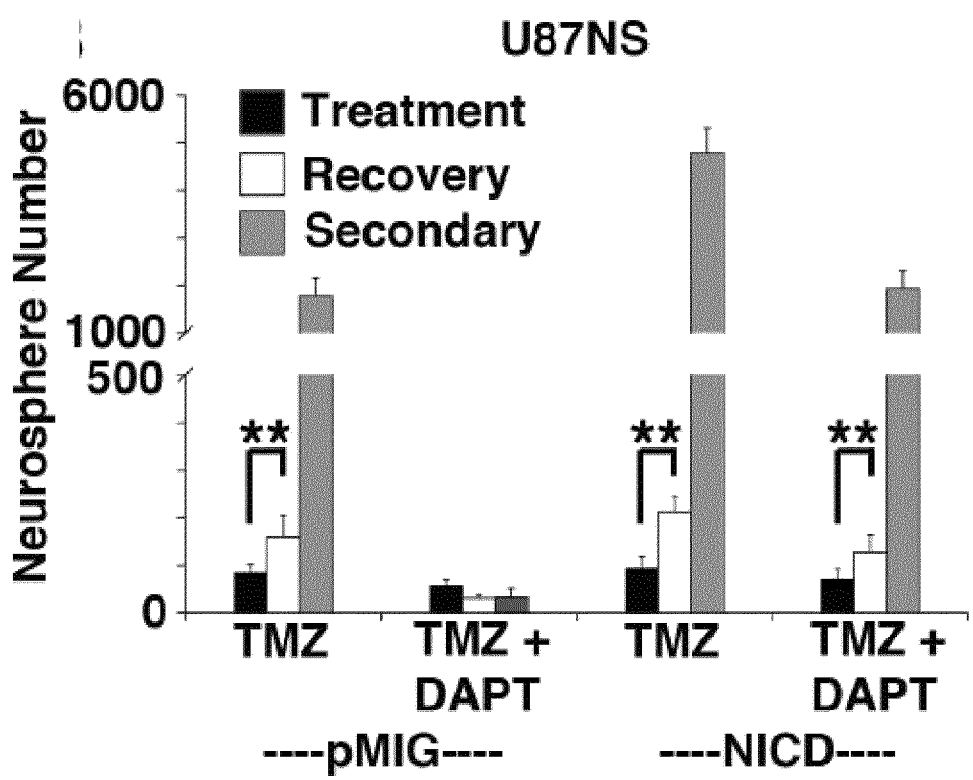
FIG. 6B is a bar graph demonstrating that treating U87NS-pMIG with TMZ+DAPT inhibited recovery, but U87NS-NICD cultures recovered after both TMZ-only and TMZ+DAPT treatment.
Figure 6C:
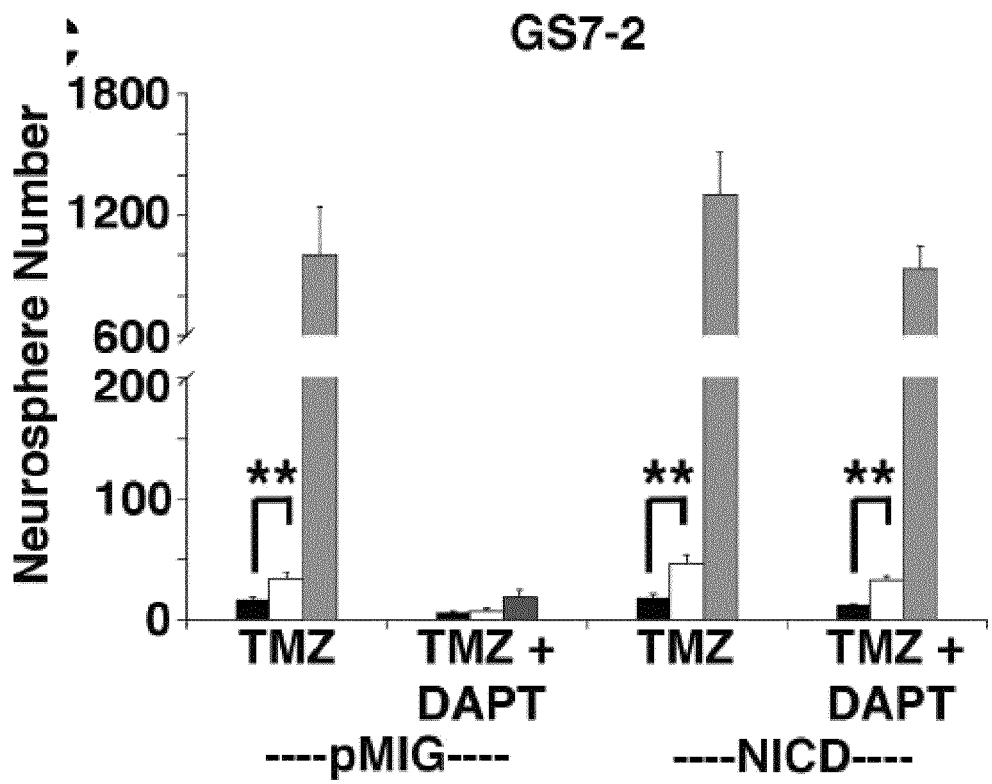
FIG. 6C is a bar graph demonstrating that in GS7-2-pMIG and GS7-2-NICD cultures treated with TMZ-only or TMZ+DAPT, cultures constitutively expressing NICD, but not the empty vector, were able to recover after TMZ+DAPT treatment. **=P<0.0001.
Figure 6D:
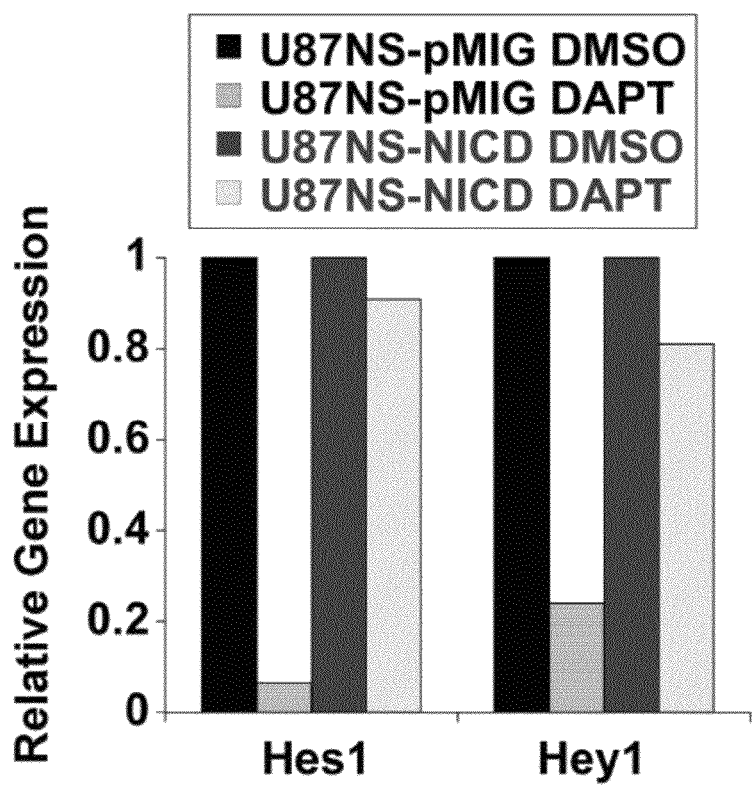
FIG. 6D is a bar graph demonstrating that DAPT does not inhibit the Notch pathway in neurospheres constitutively expressing NICD. U87NS-pMIG and U87NS-NICD cells were treated with 1 μM DAPT and collected 48 hours after treatment. qRT-PCR analysis demonstrated that Hes1 and Hey1 expression decreased in the representative DAPT treated samples. However, U87NS-NICD culture had a minimal decrease of Hes1 and Hey1 expression in the DMSO and DAPT treated samples.

Expression of functional NICD was confirmed by measuring increased mRNA levels of the downstream targets, Hes1 and Hey1 (FIG. 4A). When NICD is constitutively expressed, the Notch pathway is not inhibited by GSI treatment (FIG. 6D). NICD-expressing U87NS and GS7-2 cells treated with TMZ-only were capable of recovery and robust secondary neurosphere formation, similar to the control cells expressing the empty vector (pMIG) (FIGS. 6B and 6C). Importantly, NICD expression attenuated the effects of TMZ+DAPT treatment, and the culture demonstrated neurosphere recovery and robust secondary neurosphere formation. The control U87NS-pMIG TMZ-only treated cells had a 1.9-fold recovery, but no increase was seen in the TMZ+DAPT treated culture (FIG. 6B). U87NS-NICD cells showed a 2.3-fold recovery in TMZ-only treated cultures and a 1.8-fold recovery in TMZ+DAPT treated cultures. GS7-2-pMIG TMZ-only treated cells showed a 2.1-fold increase in neurospheres during recovery, while TMZ+DAPT treated cells showed no recovery (FIG. 6C). GS7-2-NICD cells showed a 2.6-fold recovery after TMZ-only a 2.8-fold recovery after TMZ+DAPT treatment.

Similar to the parental lines (FIGS. 5A, C), U87NS-pMIG and GS7-2-pMIG cultures treated with TMZ-only had robust secondary neurosphere formation, but cultures treated with TMZ+DAPT had minimal secondary neurosphere formation (FIG. 6B, C). In contrast, U87NS-NICD and GS7-2-NICD cultures had robust secondary neurosphere formation for both TMZ-only and TMZ+DAPT treatments. When treated with TMZ+DAPT, U87NS-NICD secondary neurosphere formation was 61.2-fold greater (P<0.0001) than U87NS-pMIG secondary neurosphere formation (FIG. 6B). In the GS7-2-NICD TMZ+DAPT treated cultures, secondary neurosphere formation was 47.8-fold greater (P<0.0001) than secondary neurosphere formation in the GS7-2-pMIG TMZ+DAPT treated cultures (FIG. 6C). Hence, constitutive NICD expression eliminates GSI enhancement of TMZ therapy, identifying the Notch pathway as the relevant GSI target.

Example 5

Figure 7A:
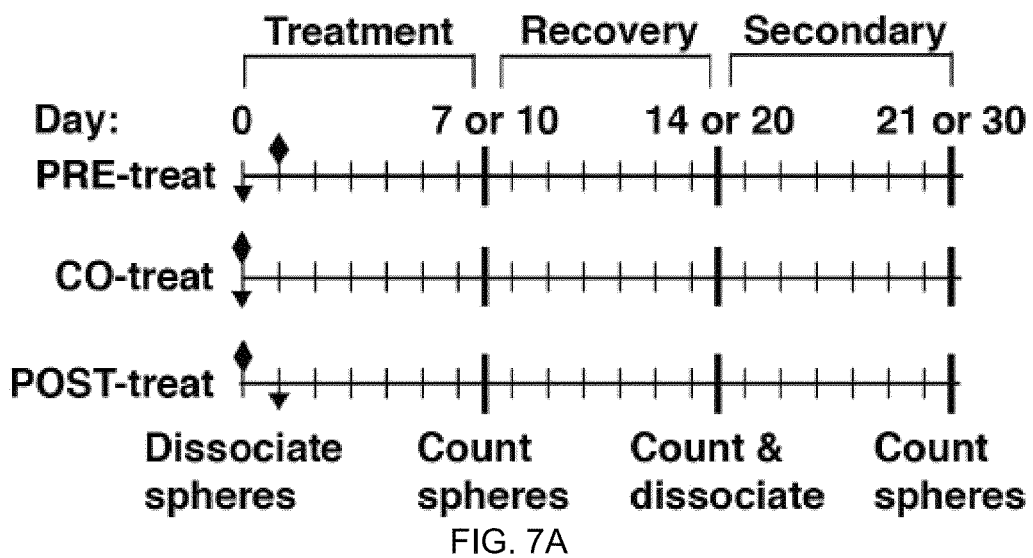
FIG. 7A is a schematic of the recovery assay treatment schedules. TMZ (diamond) and DAPT (inverted triangle) treatments were either administered with DAPT 24 hours prior to TMZ (PRE-treat), simultaneously with TMZ (CO-treat), or 24 hours after TMZ (POST-treat).
Figure 7B:
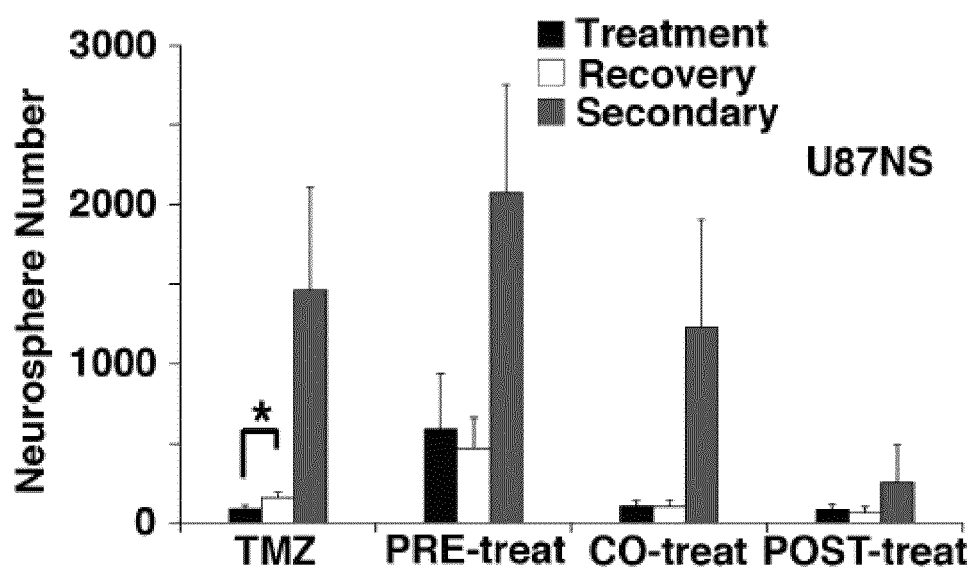
FIGS. 7B and 7C are bar graphs demonstrating that the treatment schedule of DART and TMZ affects neurosphere recovery. U87NS cultures (7B) and GS7-2 cultures (7C) were treated with different DAPT treatment schedules and recovery was analyzed. Initial neurospheres were counted on day 7 or 10 (mean±SD), recovery neurospheres were counted on day 14 or 20, and secondary neurospheres were counted on day 21 or 30. Secondary neurosphere formation was inhibited only in cultures treated with the POST-treat schedule. The t-test was used to calculate statistical significance. *=P<0.001.
Figure 7C:
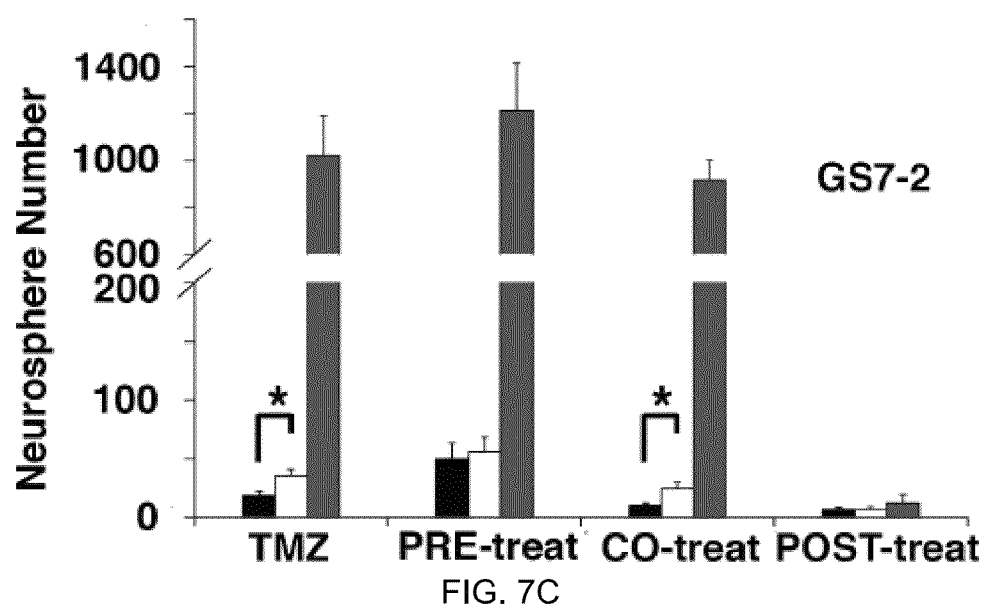

Treatment Schedules for Single Doses of TMZ and DAPT Affect Neurosphere Recovery We tested if single DAPT doses administered before, during, or after TMZ treatment would have distinct effects. TMZ and DAPT were administered to U87NS and GS7-2 neurosphere cultures with three treatment schedules (FIG. 7A). Interestingly, PRE-treatment with DAPT decreased the efficacy of TMZ. Initial neurosphere formation was 7.2-fold and 2.7-fold greater than neurosphere formation in TMZ-only treated U87NS and GS7-2 cultures, respectively (FIGS. 7B and C). When dissociated, the PRE-treated and CO-treated samples formed a large number of secondary neurospheres; however, POST-treated samples had minimal secondary neurosphere formation (FIGS. 7B and C). Secondary neurosphere formation was significantly greater in TMZ-only, PRE-treated and CO-treated cultures compared to POST-treated cultures. Secondary neurosphere formation in U87NS cultures was 5.7-fold greater (P<0.001.) with TMZ-only treatment, 8.1-fold greater (P<0.001) with DAPT PRE-treatment, and 4.8-fold greater (P<0.01) with CO-treatment, relative to secondary neurosphere formation after DAPT POST-treatment (FIG. 7B). The inhibition of GS7-2 secondary neurosphere formation was also greatest with POST-treatment. Secondary neurosphere formation in the GS7-2 cultures was 85.7-fold greater (P<0.0001) with TMZ-only treatment, 98.5-fold greater (P<0.0001) with DAPT PRE-treatment, and 72.8-fold greater (P<0.0001) with CO-treatment, when compared to the DAPT POST-treatment (FIG. 7C). These results led to two observations. First, TMZ+

DAPT treatment acts through a specific, sequence-dependent mechanism. Second, these results provide insight for in vivo treatment schedule.

Example 6

TMZ+DAPT Ex Vivo Treatment Greatly Reduces Tumor Initiation

We tested if neurosphere recovery correlated with the ability of cells to initiate tumors in a subcutaneous xenograft model.

Figure 8A:
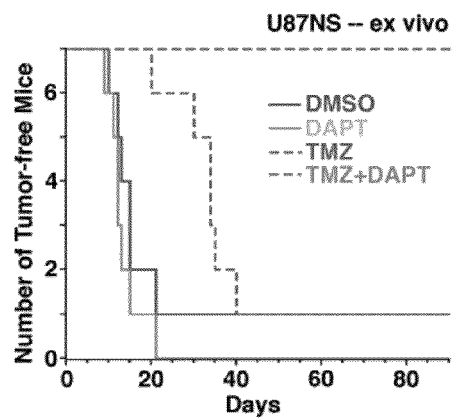
FIGS. 8A-D are line graphs (8A-C) and a dot graph (8D) showing that TMZ+DAPT treatment decreases tumorigenicity. 8A, U87NS cells were treated ex vivo with DMSO, DAPT 1 µM, TMZ 200 µM or TMZ 200 µM+DAPT 1 µM, and 7 days post-treatment, mice were subcutaneously injected with 2.5× $10^5$ live cells. TMZ treatment increased latency, but xenografts still formed. TMZ+DAPT inhibited xenograft formation. 8B, U373NS cells were treated ex vivo, and mice were subcutaneously injected with 3×10$^6$ live cells. TMZ 200 µM treatment increased latency, but tumors still formed. TMZ 200 µM+DAPT 5 µM treatment decreased xenograft formation. 8C, In vivo TMZ treatment increased the tumor latency in U87NS xenografts, but 100% of the mice succumbed to progression. TMZ+LY chow treatment completely blocked progression in 50% of the mice. 8D, Tumor volumes at the time sacrifice. The U87NS TMZ+LY chow treated xenografts that lacked progression had no palpable tumor at 150 days post-treatment.

U87NS cells were treated in vitro as follows. The cells were dissociated and $2.5 \times 10^4$ cells/ml were plated defined media and treated with DMSO, TMZ-only (200 µM), DAPT-only (1 µM or 5 µM), or TMZ+DAPT as described for recovery assays (FIG. 8A and Table 1). After 7 days, $2.5 \times 10^5$ live cells were counted using trypan blue and re-suspended in 100 µl PBS and subcutaneously injected into nude mice. Mice were monitored for tumor formation for up to 120 days post-injection and euthanized when tumors reached volumes of 1.5 to 2 cm3. Tumor initiation was observed when a palpable tumor formed. DMSO and DAPT-only ex vivo treated cells showed similar tumor incidence (6/7 and 7/7, respectively) and average latencies of 15 and 14 days, respectively. TMZ-only treated cells had an increased tumor latency of 32 days, but the tumor incidence (6/7 mice) was similar to control xenografts. Impressively, none of the mice injected with TMZ+DAPT treated cells (0/7 mice) formed tumors, even after 90 days. When a higher number of live U87NS cells ($3 \times 10^6$) were injected, we saw a similar trend (Table 1). Mice with $3 \times 10^6$ cells for U87NS DMSO (2/2 mice) and DAPT-only (2/2 mice) xenografts developed palpable tumors at 3 and 4 days, respectively, and 3/4 mice formed tumors in TMZ-only treated cells with an average latency of 25 days. With this higher number of cells injected, U87NS TMZ+DAPT xenografts formed tumors in only 1/4 mice with a longer latency of 43 days.

U87NS and U373NS neurospheres were dissociated and $2.5 \times 10^4$ cells/ml were plated in defined media and treated with DMSO, TMZ-only (200 µM), DAPT-only (1 µM or 5 µM), or TMZ+DAPT as described for recovery assays. After 7 days, $3 \times 10^6$ live cells were counted using trypan blue and re-suspended in 100 µl PBS. Cells were subcutaneously injected into the flanks of nude mice. Mice were monitored for tumor formation for up to 120 days post-injection and euthanized when tumors reached volumes of 1.5 to 2 cm$^3$.

Figure 8C:
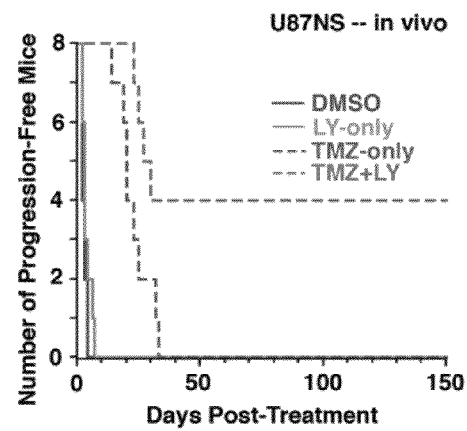
Figure 8B:
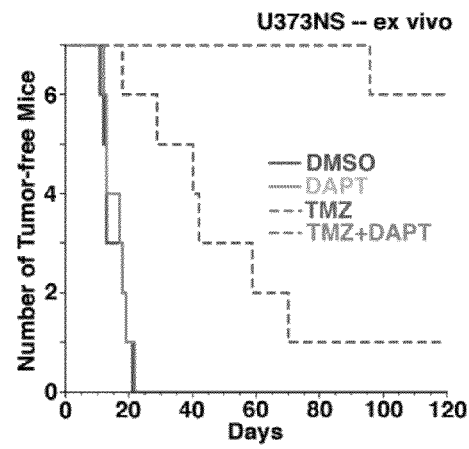

U373NS neurospheres were dissociated and $2.5 \times 10^4$ cells/ml were plated in defined media and treated with DMSO, TMZ-only (200 µM), DAPT-only (1 µM or 5 µM), or TMZ+DAPT (FIG. 8B and Table 1). After 7 days, $3 \times 10^6$ live cells were re-suspended in 100 µl PBS. Cells were subcutaneously injected into the flanks of nude mice. Mice were monitored for tumor formation for up to 120 days post-injection and euthanized when tumors reached volumes of 1.5 to 2 cm$^3$. The control DMSO cells formed palpable tumors in an average of 15 days for 7/7 xenografts, and DAPT-only treated cells formed tumors in an average of 16 days for 7/7 xenografts. Ex vivo treatment with TMZ-only increased the latency of tumor formation; however, the tumor incidence was similar to the DMSO control xenografts. Palpable tumors formed for 6/7 TMZ-treated U373NS xenografts in an average of 43 days. Ex vivo treatment with TMZ+DAPT greatly reduced tumor formation in mice. Only 1/7 mice formed a tumor in the TMZ+DAPT U373NS xenografts with an extended latency of 96 days. The tumor-free mice were observed for up to 120 days before sacrifice. These ex vivo experiments demonstrate the potency of TMZ+DAPT combined treatment in reducing tumor formation.

TABLE 1

Ex vivo Treated Xenograft Incidence and Average Latency (days)

| | U87NS | | U373NS |
|---|---|---|---|
| | $2.5 \times 10^5$ | $3 \times 10^6$ | $3 \times 10^6$ |
| DMSO | 6/7 (15) | 2/2 (3) | 7/7 (15) |
| DAPT | 7/7 (14) | 2/2 (4) | 7/7 (16) |
| TMZ | 6/7 (32) | 3/4 (25) | 6/7 (45) |
| TMZ + DAPT | 0/7 (—) | 1/4 (43) | 1/7 (96) |

Example 7

TMZ+LY In Vivo Treatment Inhibits Tumor Regrowth

We tested the effect of in vivo TMZ+GSI treatments on pre-existing subcutaneous glioma xenografts. For these in vivo experiments, we used LY411,575 incorporated into 7012 Teklad LM-485 rodent chow (LY chow) at a concentration of 0.0275 g/kg (Harlan Laboratories Inc, Madison, Wis.) (Samon et al., Blood 2008; 112: 1813-21) $10^6$ U87NS cells re-suspended in 100 µl PBS were subcutaneously injected into the flanks of male nude mice. When the tumor reached approximately 150 mm$^3$ (volume=(3/4)(π)(length/2)(width/2)$^2$), we began the following treatments: 1) DMSO control: two days of 100 µl DMSO/PBS (1:1) intraperitoneal (i.p.) injections; 2) TMZ-only: injections of TMZ (20 mg/kg) in 100 µl DMSO/PBS on days one and two; 3) LY chow-only: two days of 100 µl DMSO/PBS i.p. injections. The mice were fed LY chow from day 3 to 12; 4) TMZ+LY chow: i.p. injections of TMZ (20 mg/kg) in 100 µl DMSO/PBS on days one and two. The mice were fed LY chow from day 3 to 12. Mice were observed for up to 150 days and euthanized when the tumor reached 1.5 to 2 cm$^3$.

Figure 8D:
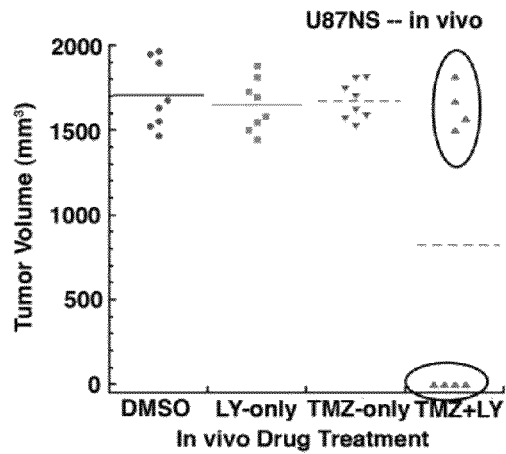
Figure 8E:
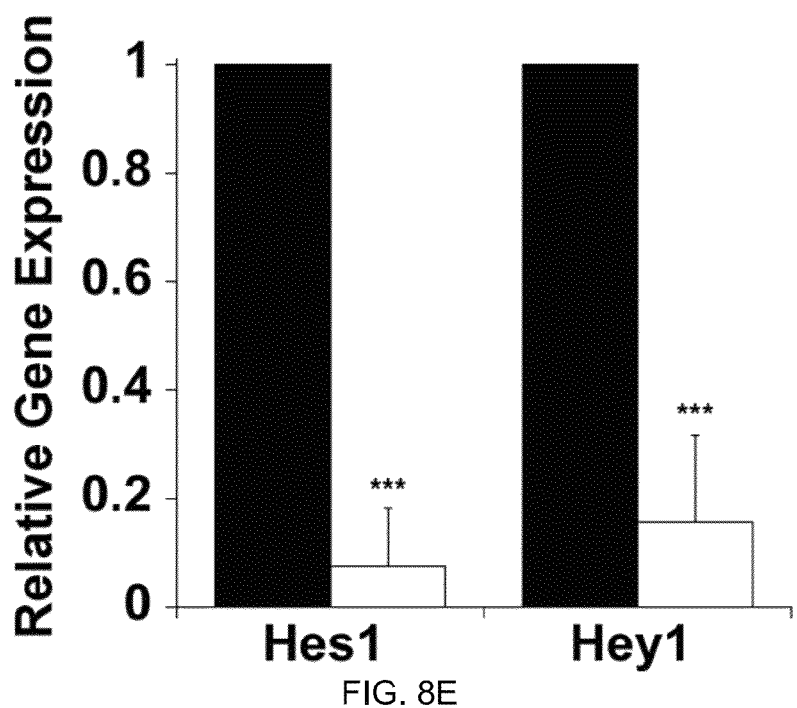
FIG. 8E is a bar graph demonstrating that LY chow significantly decreased the mRNA levels of the Notch targets Hex1 and Hey1 in glioblastoma tumors. Immunocompromised nude mice with pre-existing U87NS xenografts were given a diet of normal chow (n=4) or LY chow (n=4) for ten consecutive days. After LY treatment, mRNA was isolated from the xenografts and Notch activity was analyzed by qRT-PCR. Hes1 and Hey1 expression significantly decreased in the LY chow cohorts. ***=P<0.0001.
Figure 9A:
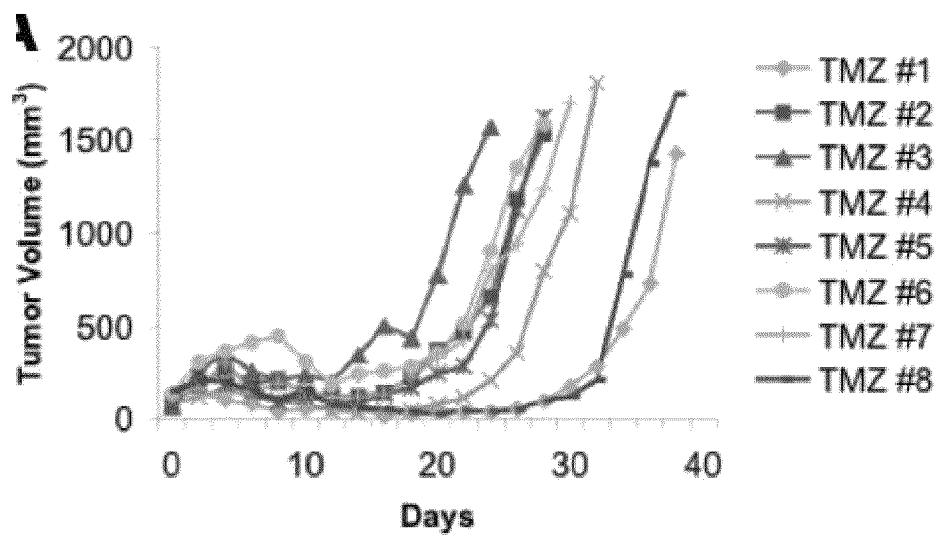
FIGS. 9A and 9B are line graphs showing individual tumor volumes for TMZ-only and TMZ+LY chow treated mice. 9A, Mice with pre-existing tumors were treated in vivo with TMZ-only when tumors reached approximately 150 mm$^3$ and observed for tumor progression, which was classified as the point when the tumor doubled in volume, approximately 300 mm$^3$. Tumors initially began to decrease in volume 5 days after the beginning of treatment. Although all TMZ-only tumors demonstrated regrowth, the time until tumor progression varied greatly between 14 to 32 days after treatment. 9B, Mice with pre-existing tumors were treated with TMZ+LY chow when the tumors reached approximately 150 mm$^3$. Tumors initially decreased in volume 5 days after the beginning of treatments. 4/8 mice demonstrated tumor progression between 23 to 30 days. The other 4/8 mice demonstrated a complete loss of tumor mass and remained at 0 mm$^3$ for 150 days after treatment until the mice were sacrificed.
Figure 9B:
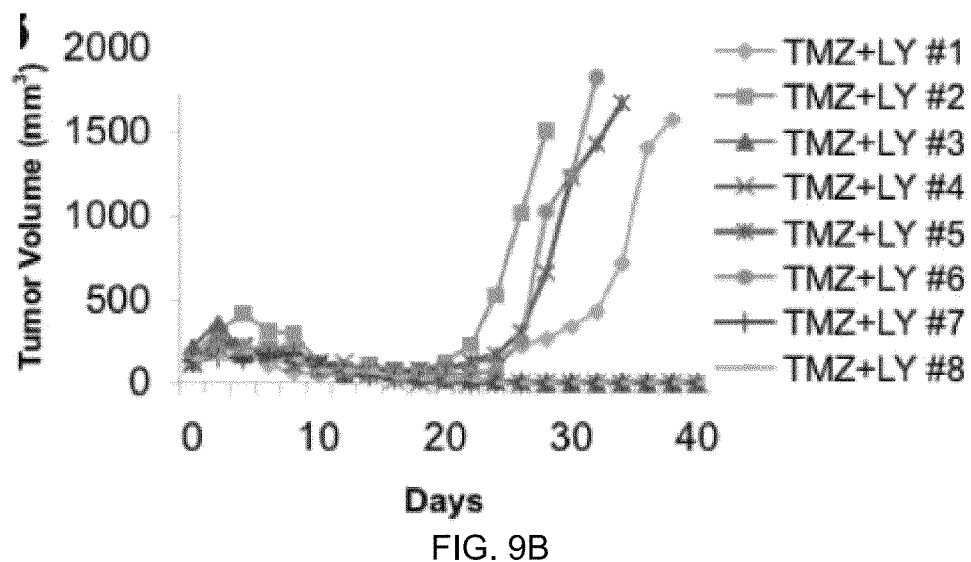

A ten-day diet of LY chow significantly decreased the mRNA levels of the Notch targets Hes1 and Hey1 (FIG. 8E). Mice were subcutaneously injected with $10^6$ U87NS cells and treated when the tumors reached a volume of approximately 150 mm$^3$. When the tumor volume was double the original volume from the start of the drug treatments, we judged the xenograft as progressing. The DMSO control and LY chow-only cohorts did not have any delay in tumor progression (FIG. 8C). TMZ treatment initially had decreased tumor volumes (FIG. 9A). However, the TMZ-only treated tumors progressed in 8/8 xenografts, and tumor volume doubled in an average of 23±7 days after treatment (FIG. 8C). These tumors had a normal growth rate and were sacrificed between 23 to 39 days post-treatment. Impressively, 4/8 the mice treated with TMZ+LY chow displayed no tumor progression (FIG. 8C). In the other 4/8 mice treated with TMZ+LY chow, tumor progression occurred in an average of 26±3 days (FIG. 9B), and mice were euthanized between 24 to 33 days post-treatment. The TMZ+LY chow mice that did not have tumor progression displayed a complete loss of a palpable tumor and remained tumor-free until euthanized at 150 days (FIG. 8D). In these mice, no tumor masses were evident by gross dissection and examination of H&E stained sections. Hence, the TMZ+LY chow treatment had a dramatic effect on pre-existing tumors by curing 50% of the mice. During drug administration, toxicity was determined by weight loss. TMZ-only and TMZ+

Figure 10:
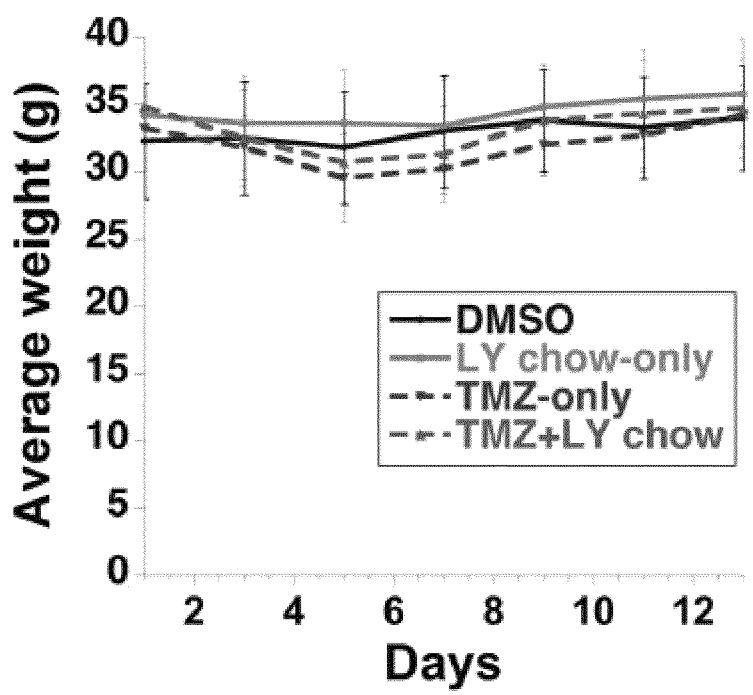
FIG. 10 is a line graph showing that TMZ+LY chow inhibits tumor progression with minimal toxicity to the immunocompromised mice. Tolerance of the drug treatments was determined by measuring the weight of the mice during the period of drug administration. Initially, TMZ-only and TMZ+LY chow cohorts demonstrate a slight decrease in body weight, but the mice quickly recover. There was no significant change in the final weight of the mice for any of the drug treatments. For DMSO, n=4; LY chow, n=5; TMZ-only; n=6; and TMZ+LY chow, n=6.

LY chow cohorts initially showed a slight weight loss after TMZ injections (FIG. 10). However, the TMZ-only and TMZ+LY chow mice returned to their starting body weight, and no significant weight difference was observed throughout the remainder of the treatment. This demonstrates that the mice tolerated the LY chow alone and the combination of the TMZ+LY chow. The lack of overall weight loss also suggests that the mice on LY chow diets did not significantly reduce their food consumption compared to control mice and received the estimated average dose of 5 mg/kg/day of LY411,575 (Samon et al., Blood 2008; 112: 1813-21).

REFERENCES

Singh S K, Clarke I D, Terasaki M, et al. Cancer Res 2003; 63: 5821-8.
Ponti D, Costa A, Zaffaroni N, et al. Cancer Res 2005; 65: 5506-11.
Ricci-Vitiani L, Lombardi D G, Pilozzi E, et al. Nature 2007; 445: 111-5.
Singh S K, Hawkins C, Clarke I D, et al. Nature 2004; 432: 396-401.
Ernst A, Hofmann S, Ahmadi R, et al. Clin Cancer Res 2009; 15: 6541-50.
Shih A H, Holland E C. Neoplasia 2006; 8: 1072-82.
Kanamori M, Kawaguchi T, Nigro J M, et al. J Neurosurg 2007; 106: 417-27.
Fischer A, Gessler M. Nucleic Acids Res 2007; 35: 4583-96.
Fan X, Khaki L, Zhu T S, et al. Stem Cells 2010; 28: 5-16.
Wang J, Wakeman T P, Lathia J D, et al. Stem Cells; 28: 17-28.
Sen A, Kallos M S, Behie L A. Tissue Eng 2004; 10: 904-13.
Liu G, Yuan X, Zeng Z, et al, Mol Cancer 2006; 5: 67.
Kang M K, Kang S K. Stem Cells Dev 2007; 16: 837-47.
Bao S, Wu Q, McLendon R E, et al, Nature 2006; 444: 756-60.
Jeon H M, Jin X, Lee J S, et al., Genes Dev 2008; 22: 2028-33.
Gilbert C A, Ross A H. J Cell Biochem 2009; 108: 1031-8.
Chalmers A J, Ruff E M, Martindale C, Lovegrove N, Short S C. Int J Radiat Oncol Biol Phys 2009; 75: 1511-9.
Kreft A F, Martone R, Porte A, J Med Chem 2009; 52: 6169-88.
Barten D M, Meredith J E, Jr., Zaczek R, Houston J G, Albright C F. Drugs R D 2006; 7: 87-97.
Wu Y, Cain-Hom C, Choy L, et al. Nature 2010; 464: 1052-7.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating glioblastoma in a subject, the method comprising:
   selecting a subject who is in need of treatment for glioblastoma;
   administering to the subject a therapeutically effective amount of temozolomide; and
   administering to the subject a therapeutically effective amount of a gamma secretase inhibitor at least 24 hours after administering the temozolomide,
   thereby treating the glioblastoma in the subject.

2. The method of claim 1, wherein the gamma secretase inhibitor is selected from the group consisting of semagacestat; LY411575; N-[N-(3,5-difluorophenacetyl)-L-alanyl]-(S)-phenylglycine t-butyl ester (DAPT); Compound E; L-685,458; BMS-299897; MK0752; and MRK-003.

3. The method of claim 2, wherein the gamma secretase inhibitor is LY411575.

4. The method of claim 1, comprising administering two or more doses of the temozolomide.

5. The method of claim 1, comprising administering two or more doses of the gamma secretase inhibitor.

6. The method of claim 2, wherein the gamma secretase inhibitor is semagacestat.

7. The method of claim 2, wherein the gamma secretase inhibitor is DAPT.

8. A method of treating glioblastoma in a subject, the method comprising:
   selecting a subject who is in need of treatment for glioblastoma;
   administering to the subject a therapeutically effective amount of temozolomide; and
   administering to the subject a therapeutically effective amount of a gamma secretase inhibitor selected from the group consisting of semagacestat, LY411575, and N-[N-(3,5-difluorophenacetyl)-L-alanyl]-(S)-phenylglycine t-butyl ester (DAPT);
   thereby treating the glioblastoma in the subject.

9. The method of claim 8, wherein the gamma secretase inhibitor is administered after the temozolomide.

10. The method of claim 9, wherein the gamma secretase inhibitor is administered at least 24 hours after administering the temozolomide.

11. The method of claim 8, comprising administering two or more doses of the temozolomide.

12. The method of claim 8, comprising administering two or more doses of the gamma secretase inhibitor.

13. The method of claim 8, wherein the gamma secretase inhibitor is semagacestat.

14. The method of claim 8, wherein the gamma secretase inhibitor is LY411575.

15. The method of claim 8, wherein the gamma secretase inhibitor is DAPT.

* * * * *